United States Patent
Rohayem

(10) Patent No.: US 10,023,871 B2
(45) Date of Patent: Jul. 17, 2018

(54) DOUBLE-STRANDED POLYC:POLY(G/I) RNA FOR IMMUNOSTIMULATION AND CANCER TREATMENT

(71) Applicant: RiboxX GmbH, Radebeul (DE)

(72) Inventor: Jacques Rohayem, Dresden (DE)

(73) Assignee: RiboxX GmbH (DE)

( * ) Notice: Subject to any disclaimer, the term of this patent is extended or adjusted under 35 U.S.C. 154(b) by 0 days.

(21) Appl. No.: 15/105,467

(22) PCT Filed: Dec. 16, 2014

(86) PCT No.: PCT/EP2014/078100
§ 371 (c)(1),
(2) Date: Jun. 16, 2016

(87) PCT Pub. No.: WO2015/091578
PCT Pub. Date: Jun. 25, 2015

(65) Prior Publication Data
US 2016/0312224 A1    Oct. 27, 2016

(30) Foreign Application Priority Data

Dec. 16, 2013    (EP) ..................................... 13197558

(51) Int. Cl.
| | | |
|---|---|---|
| C07H 21/02 | (2006.01) | |
| A61K 48/00 | (2006.01) | |
| C12N 15/117 | (2010.01) | |
| A61K 39/39 | (2006.01) | |
| A61K 45/06 | (2006.01) | |
| C12P 19/34 | (2006.01) | |
| A61K 39/00 | (2006.01) | |

(52) U.S. Cl.
CPC ............ *C12N 15/117* (2013.01); *A61K 39/39* (2013.01); *A61K 45/06* (2013.01); *C12P 19/34* (2013.01); *A61K 2039/55561* (2013.01); *C12N 2310/17* (2013.01); *C12N 2310/331* (2013.01); *C12N 2310/351* (2013.01); *C12N 2310/53* (2013.01); *C12N 2310/533* (2013.01); *C12N 2330/50* (2013.01)

(58) Field of Classification Search
CPC .. C12N 15/113; C12N 2310/11; A61K 31/713
See application file for complete search history.

(56) References Cited

FOREIGN PATENT DOCUMENTS

| WO | 2008017473 A2 | 2/2008 |
| WO | 2011059505 A2 | 5/2011 |
| WO | 2013064584 A1 | 5/2013 |

OTHER PUBLICATIONS

Vil'ner, et al.; "Anti Viral and Interferonogenic Activity of Synthetic Complexes of Homo Poly Ribo Nucleotides and Complexes of Homo and Hetero Poly Ribo Nucleotides", (1977) Vestnik Adakemii Meditsinskih NAUK SSR No. 5, pp. 64-70.
Brabec, et al., ; "Electrochemistry of Double-Stranded Complexes of Synthetic Polyribonucleotides Having Interferonogenic and Antiviral Activity", Gen. Physiol. Bipphys (1983). 2, 487-497.
Clercq, et al.; "Interferon induction by mismatched analogues of polyinosinic acid . polycytidylic acid [(Ix,U)n.(C)n]", Nucleic Acids Research, vol. 7, No. 7 1979. pp. 2003-2014.
Patel, et al.; "Toll-like receptor 3 (TLR3) protects retinal pigmented epithelium (RPE) cells from oxidative stress through a STAT3-dependent mechanism", Mol Immunol. Jun. 2013; 54(2): 122-131.

*Primary Examiner* — Amy H Bowman
(74) *Attorney, Agent, or Firm* — St Onge Steward Johnston and Reens LLC

(57) ABSTRACT

The present invention relates to polyC:poly(G/I) dsRNAs for triggering innate immunity, in particular through toll-like receptor 3 (TLR-3) and, optionally, RIG-I or RIG-I-like receptors (RLRs), as well as compositions and medicaments containing such dsRNAs, methods for their production and their use in medicine, especially immunostimulation and prevention and/or therapy of infections and tumor diseases.

30 Claims, 30 Drawing Sheets

DOUBLE-STRANDED POLYC:POLY(G/I) RNA FOR IMMUNOSTIMULATION AND CANCER TREATMENT

FIELD OF THE INVENTION

The present invention relates to polyC:poly(G/I) dsRNAs for triggering innate immunity, in particular through toll-like receptor 3 (TLR3) and, optionally, RIG-I or RIG-I-like receptors (RLRs), as well as compositions and medicaments containing such dsRNAs, methods for their production and their use in medicine, especially immunostimulation and prevention and/or therapy of infections, degenerative diseases and tumor or cancer diseases.

BACKGROUND OF THE INVENTION

In the initial phase of infection, the innate immune system generates a rapid and potent inflammatory response. This response aims at blocking dissemination of the infectious agent, with subsequent activation of T cells and B cells that provide the acquired immune response against the pathogen. Recognition of pathogen-related components by immune cells occurs through pathogen recognition receptors (PRRs). PRRs are present on cell surfaces, in endosomes, and in the cytosol. Toll-like receptors (TLRs) represent an important family of PRRs (see, e.g., Gay and Gangloff (2007) Ann. Rev. Biochem. 76, 141-1659). TLRs are expressed on various subsets of immune cells such as dendritic cells (DCs), monocytes and macrophages. DCs and macrophages as well as monocytes are professional antigen-presenting cells that play an important role in the induction and maintenance of innate and adaptive immune responses. Due to their functional properties and prominent expression of TLRs, DCs represent promising candidates for TLR agonist-based vaccination strategies against tumors and pathogens (reviewed in, e.g., Palucka and Banchereau (2012) Nature Reviews Cancer 12 (4), 265-277).

Polyinosinic:polycytidylic acid (poly(I:C)) is a potent activator of innate immunity (Field et al. (1967) Proc. Natl. Acad. Sci. U.S.A., 58, 1004-1010) and a potent inducer of apoptosis in cancer or tumor cells (melanoma: Weber et al. (2010) Cell Death Differ. 17(6), 942-951; prostate cancer: Paone et al. (2008) Carcinogenesis 29(7), 1334-1342; breast cancer: Salaun et al. (2006) J. Immunol. 176(8), 4894-4901; hepatocellular carcinoma: Guo et al. (2012) Oncology Reports 27(2), 396-402; lung cancer: Estomes et al. (2012) Cell Death Differ. 19(9), 1482-1492; neuroblastoma: Chuang et al. (2011) J. Biomed Sci. 18, 65; Van et al. (2012) FASEB J. 26(8), 3188-3198). Poly(I:C) activates DCs through combined targeting of various innate immunity pathways including TLR3. Major disadvantages of poly(I:C) comprise its undefined chemical structure and very poor homogeneity which is due to its manufacturing process (Grunberg-Manago et al. (1955) Science 122 (3176), 907-910). Poly(I:C) is composed of a mixture of single-stranded and double-stranded RNAs. This is mainly due to limited solubility and difficult reconstitution of poly(I:C) that requires heating (50 to 60° C.) and slow cooling over many hours to achieve reannealing of the poly(I) and poly(C) strands. As a consequence, poly(I:C) has a reported toxicity in clinical trials, ranging from hypersensitivity to coagulopathy, renal failure, or systemic cardio-vascular failure (Robinson et al. (1976) J. Nat. Cancer Inst. 57 (3), 599-602). A further frequent problem of double-stranded RNA (dsRNA) compounds such as poly(I:C) is their rapid degradation in body fluids by RNAses, with a reported half-life of a few minutes (Levy et al. (1975) J. Inf. Dis., 132, p. 434; Bumcrot et al. (2006) Nat. Chem. Biol. 2 (12), 711-719) and subsequent unpredictable pharmacokinetics of degradation products. Optimization of physicochemical properties of poly(I:C) has led to the generation of derivatives that have increased stability in body fluids (such as polyICLC; see Levy et al. 1975, supra), or reduced toxicity through reduced stability in body fluids (such as poly(I:$C_{12}$U; see, e.g., Basani et al. (2009) Vaccine 27 (25), 3401-3404).

WO-A-2013/064584 discloses TLR3 agonists which are ribonucleic acids comprising at least one segment of double-stranded structure of at least 45 bp wherein said at least one segment of double-stranded structure has a first and a second end each having at least 3 to 10 G/C bp within the last 6 to 20, respectively, bp calculated from the last bp of the respective end of the double-stranded structure, and wherein the nucleotide sequence between the last 6 to 20 bp at each end is heteropolymeric.

Naumann et al. (2013) Clinical and Developmental Immunology, available under the URL http://www.hindawi.com/journals/cdi/2013/283649/, describe the activation of DCs through the TLR3 agonist (G:C)$_{100}$ named "RGC100".

SUMMARY OF THE INVENTION

The technical problem underlying the present invention is to provide novel TLR3 agonists having improved potency as to the activation of immune cells and/or as to induction of apoptosis of cancer or tumor cells.

The solution to the above technical problem is provided by the embodiments as described herein and in the claims.

In particular, the present invention provides dsRNAs having a length of at least 45 bp wherein one strand is polycytidylic acid (poly(C)). In other embodiments this strand is substantially composed of cytosine residues, i.e. there may be a low number of other nucleotides such as not more than 10% of the nucleotides in this strand. The other strand being complementary to the poly(C) (or substantially poly(C)) strand has a nucleotide sequence composed of guanosine (G) and inosine (I) residues according to the formula $(G)_{1\ to\ (n-1)}:I_{(n-1)\ to\ 1}$, preferably $(G)_{10\ to\ (n-10)}:I_{(n-10)\ to\ 10}$, i.e. the complementary strand has from 1 to n–1 G residues, preferably 10 to n–10 G residues (n being the total number of nucleotides in the complementary strand or length of the dsRNA, respectively), and the respective remainder are I residues, or vice versa, whereby the G and I residues can be present in any sequence, i.e. the G and I residues can be located at any position within the sequence of the complementary strand. In case, the first strand is not pure poly(C), the complementary strand has complementary nucleotides in those positions in which on the first strand a non-cytosine residue is present whereas the remaining residues of the complementary strand comply with the above formula (wherein in this case n is the number of C residues in the first strand). In further preferred embodiments, the complementary strand of dsRNAs of the invention has an inosine content of from about 1 to about 99%, more preferably about 5 to about 95%, most preferred from about 10 to about 80%.

In preferred embodiments, the strand complementary to the poly(C) strand contains more I residues than G residues, e.g. the ratio of G to I residues in the complementary strand is about 1:2 or lower such as about 1:3, about 1:4 or about 1:5. In other preferred embodiments of this type, the inosine content in the complementary strand is about 51 to about 90%, particularly preferred about 51 to about 80%, more preferably about 51 to about 60%. Highly preferred examples of dsRNAs according to the invention have an inosine content in the complementary strand of about 56%.

In other preferred embodiments of the invention, the strand complementary to the poly(C) strand contains more G residues than I residues, e.g. the ratio of G to I residues in the complementary strand is about 2:1 or higher such as about 3:1, about 4:1 or about 5:1. In yet other preferred embodiments, the amount of G and I residues is approximately equal, i.e. the molar ratio of G to I residues in the complementary strand is about 1:1.

In contrast to poly(I:C), the dsRNAs of the present invention have a defined chemical composition and molecular weight, and also show a superior solubility in aqueous media. Moreover, as shown in the below Examples, dsRNAs of the invention have an increased potency in triggering an innate immune response in comparison to prior art TLR3 agonists such as those described in Nauman et al. (2013), supra, or WO-A-2013/064584. Very surprising, preferred embodiments of the dsRNAs according to the invention have an even stronger potency of generating innate immunity in comparison to poly(I:C).

In other embodiments of the invention, the above dsRNA can represent only a segment of a larger nucleic acid. Thus, according to certain embodiments of the invention, the dsRNA as defined above may also have overhangs at one or both ends, and at the 5' or 3' end(s) of the double-stranded structure, which can be of various length but typically do not exceed ten single-stranded residues, more preferably such overhangs comprise one, two or three residues. These overhangs may also comprise deoxyribonucleotides instead of ribonucleotides.

For effectively triggering TLR3, the dsRNA of the invention has a length of at least 45, preferably at least 50 bp, more preferably of at least 70 bp, particularly preferred of from 45, 46, 47, 48, 49 or 50 to 200 bp or even more bp, most preferably from about 50 to about 100 bp. Especially preferred embodiments of the dsRNAs according to the invention have lengths of 50 bp or multiplicities of 50 bp such as 100 bp, 150 bp, 200 bp, 250 bp etc., whereby lengths of 100 bp, 150 bp and 200 bp are particularly preferred.

Further preferred dsRNAs of the invention have a free triphosphate group at the 5'-end of at least one strand. Such triphosphate-containing dsRNAs of the invention are preferably completely double-stranded and one or both 5' ends contain(s) a free triphosphate group (in general, at least the 5' end containing the 5'-triphosphate group should be a blunt end). A "free triphosphate group" in this context means that this triphosphate group is not modified and specifically does not contain, or is not part of, respectively, a cap structure. Such triphosphate-containing RNAs of the invention are particularly potent immunostimulative compounds.

A free triphosphate-containing double-stranded ribonucleic acid of the present invention triggers both RIG-I and/or RIG-I-like receptors also known as RLRs (see. e.g. WO 2008/017473 A2) and TLR-3 pathways and exerts a dose-dependent activation of an innate immune response.

In further embodiments the dsRNAs according to the invention can be conjugated to other chemical or biological entities. Such ligands may be attached to the dsRNA by chemical or other bonds such as hydrogen bonds or Van der Waals bonds. Preferred ligands bound to the dsRNA are selected from the group consisting of dyes, fluorescent labels, proteins such as antigens or antibodies and antibody fragments. The antibody may be monoclonal or polyclonal. The antibody may be chimeric or humanized. The antibody may be a single chain antibody. The antibody fragment may be a Fab fragment, a F(ab')$_2$ fragment, or any fragment that retains the antigen-binding specificity of the intact antibody. The ligand may be coupled to the dsRNA either directly or through a linker, typically a short peptide, carbohydrate or hydrocarbon moiety, polyethyleneglycol (PEG) or a member of a non-covalent binding partner such as biotin or digoxigenin, as appropriate. Especially preferred antibody ligands that may be coupled to the dsRNA are selected from antibodies or fragments thereof directed against tumor antigens, tumor-associated antigens or onoproteins, or antigens present on non-tumoral cells.

The invention is also directed to derivatives of the dsRNAs as defined herein which carry reactive groups, e.g. for coupling linkers or ligands, preferably as outlined above. Reactive groups in this context preferably include thiol groups, amino groups and maleimide groups which may be present at any part of the molecule such as one or more bases, or at the 3' and/or 5' end of one or both strands.

Further subject matter of the invention is a composition comprising at least two different dsRNAs as defined above, wherein the dsRNAs differ in their base composition and/or their length. Accordingly, the invention also comprises mixtures or pools, respectively, of at least two or multiple dsRNAs as defined herein.

Particularly preferred are compositions of dsRNAs of equal length but different base compositions wherein it is understood that each of the dsRNAs in the composition complies with the above definition. This means that, with respect to the individual dsRNAs as defined above in the composition, the molar percentage (mol-%) of cytosine residues is 50% (or almost 50% in case a minor number of non-cytosine residues are present, as outlined above) whereas the percentage of guanosine and inosine residues, respectively, varies. However, with respect to the overall base percentages, an individual composition can be identified and pre-selected, i.e. the overall (i.e. average) base percentages of the bases C, G and I result from the accumulated base compositions of all individual dsRNAs present in the composition of the invention.

Preferred base percentages (accumulated over all individual dsRNAs) of G and I, respectively, in the compositions of the invention range from about 1 to about 49 mol-% G, more preferably about 1 to about 45 mol-% G, even more preferred about 5 to about 45 mol-%, particularly preferred about 10 to about 40 mol-% G and the remainder I, or vice versa, and the mol-percentage of C is 50 mol-%. Especially preferred are dsRNA compositions in which the base percentage of I residues is higher than the percentage of G residues, e.g. compositions having a base composition of about 26 to about 49 mol-% I, 50 mol-% C, and the remainder G, more preferably about 26 to 40 mol-% I, most preferably from about 28 to about 39 mol-% I (e.g. about 28 mol-%, about 36 mol-%, or about 39 mol-% I), 50 mol-% C, and the respective remainder G. In especially preferred embodiments, the molar ratio of G to I is about 1:2 or lower, such as about 1:3, about 1:4 or about 1:5.

Double-stranded RNAs according to the invention may be prepared through chemical synthesis or enzymatically using biocatalysts in a known fashion.

Compositions as defined above, in particular compositions containing dsRNAs of the invention of equal length but differing in their base composition, are preferably prepared enzymatically using RNA-dependent RNA polymerases (RNAses) from a virus of the Caliciviridae family. This embodiment of the invention typically comprises the step of incubating a single-stranded poly(C) ssRNA template (usually of defined length) in the presence of a calicivirus RdRp and in the presence of rGTP and rITP. The further incubation conditions (time, temperature, buffer conditions etc.) in order to provide appropriate conditions for RNA synthesis on the poly(C) template to occur are known to the skilled person (see, e.g., WO-A-2007/012329, WO-A-2009/150156). The molar ratio of rGTP to rITP in said mixture is preferably from about 1:10 to about 10:1, more preferably from about 1:4 to about 4:1, so as to provide the desired relative amounts of G and I residues in the dsRNA(s).

Furthermore, e.g. to simplify the introduction of ligands (or at least of a linker moiety, as a pre-step for the introduction of a ligand), the above method may be carried out in the presence of an appropriate primer, such as an oligo(G) primer or a primer having a mixed sequence of G and I residues.

Enzymatic methods for preparing dsRNAs or, as outlined above, compositions thereof using calicivirus RdRps may also be used to introduce modified or labeled rGTP/rITP into the dsRNAs, as described previously; see WO-A-2009/150156.

Accordingly, the dsRNAs of the invention or contained in the compositions as described herein may contain one or more modified nucleotide analogues, in particular based upon stability considerations.

The chemical modification of the nucleotide analogue in comparison to the natural occurring nucleotide may be at the ribose, phosphate and/or base moiety. With respect to molecules having an increased stability, especially with respect to RNA degrading enzymes, modifications at the backbone, i.e. the ribose and/or phosphate moieties, are especially preferred.

Preferred examples of ribose-modified ribonucleotides are analogues wherein the 2'-OH group is replaced by a group selected from H, OR, R, halo, SH, SR, $NH_2$, NHR, $NR_2$, or CN with R being $C_1$-$C_6$ alkyl, alkenyl or alkynyl and halo being F, Cl, Br or I. It is clear for the person skilled in the art that the term "modified ribonucleotide" also includes 2'-deoxyderivatives, such as 2'-O-methyl derivatives, which may at several instances also be termed "deoxynucleotides".

As mentioned before, the at least one modified ribonucleotide may be selected from analogues having a chemical modification at the base moiety. Examples of such analogues include, but are not limited to, 6-aza-uridine, 7-deaza-guanine, and 5-methyl-cytidine.

Examples of backbone-modified ribonucleotides wherein the phosphoester group between adjacent ribonucleotides is modified are phosphothioate groups.

The present invention is also generally directed to enzymatic synthesis methods providing RNA molecules containing inosine residues. Thus, as a further aspect of the invention, there is provided a method for synthesizing an RNA molecule containing at least one inosine residue comprising the steps of
(a) providing an ssRNA template (single-stranded RNA template) containing at least on C ribonucleotide; and
(b) incubating the ssRNA template with an RNA-dependent RNA polymerase (RdRp) from a calicivirus under conditions sufficient for RNA synthesis in the presence of an rNTP mixture comprising rITP.

Also in the above step (b) a primer, which has been pre-annealed to the template, may be present or not.

In order to produce ssRNA containing inosine residues (or at least one thereof) the generated strands containing the inosine residue(s) can be separated from the template strand(s) by known means, i.e. through heating, chemical denaturation or enzymatically through an enzymatic activity capable of separating dsRNA into ssRNA such as a helicase activity.

In the methods of the invention, it is also contemplated to repeatedly separate the dsRNA into single strands and repeating the RNA synthesis step(s) such that an amplification of the resulting dsRNA occurs.

Caliciviral RdRps for use in the present invention are known in the art, and specific members, in particular from Sapovirus or Norovirus are disclosed in WO-A-2007/012329, WO-A-2009/150156, WO-A-2011/048193, and WO-A-2011/048198. In this respect, it is particularly referred to the Sapovirus RdRp proteins disclosed in theses references.

Further subject matter of the present inventions relates to medicaments, i.e. pharmaceutical compositions, comprising the dsRNA or compositions thereof as defined above together with at least one pharmaceutically acceptable carrier, excipient and/or diluent.

Thus, the dsRNAs or compositions of such dsRNAs as defined or disclosed above are particularly for use as agonists of TLR-3. Further preferred dsRNAs of the invention containing a free 5'-triphosphate moiety are also agonists of RIG-I and/or RIG-I-like receptors (RLRs). In that function, the RNA molecules of the present invention exert an immunomodulatory effect, more preferably an immunostimulatory effect in immune and non-immune cells, tissues or organisms. Furthermore, dsRNAs of the invention can trigger a pro-apoptotic effect in cancer or tumor cells, either in single cells, tissues, organs or organisms. dsRNAs and their compositions according to the present invention are therefore useful as medicaments, in particular immunomodulatory preparations, preferably immunostimulatory preparations, as well as tumor and/or cancer cell pro-apoptotic preparations. The dsRNAs are also suitable to be used in the prevention and/or treatment of degenerative diseases such as acute macular degeneration (AMD) which is preferably treated by intra-ocular injection of an effective amount of a pharmaceutical composition as defined herein. dsRNAs and compositions thereof according to the invention are also contemplated for the manufacture of a medicament for immunomodulation, in particular immunostimulation, and for prevention and/or treatment of tumors and/or cancer and/or degenerative diseases. The preparation of pharmaceutical compositions in the context of the present invention, their dosages and their routes of administration are known to the skilled person, and general guidance can be found in the latest edition of Remington's Pharmaceutical Sciences (Mack Publishing Co., Eastern, Pa., USA).

Preferred pharmaceutical compositions are injectable solutions containing the dsRNAs or their compositions as defined above, optionally in combination with one or more antigens of interest, and, if desired or required, further adjuvants or other typical components of immunomodulatory preparations, preferably immunostimulatory preparations, or anti-cancer/anti-tumor preparations, in (preferably pyrogen-free) water, isotonic aqueous media (such as Ringer lactate or isotonic NaCl solution) or buffer to provide the appropriate pH value.

In cases where the RNA of the invention is used as an immunostimulatory drug alone, a topical administration of the appropriate preparation (e.g. a spray or an injectable solution) to skin and/or mucosa is preferred. As an "RNA drug" the RNA of the present invention leads to stimulation of antigen-presenting cells such as dendritic cells, monocytes and macrophasges and generation of a CD8+ T cell response, NK cell response and/or B cell response leading to antibody production. Such stimulation of immune and/or non-immune cells typically leads to the induction of type I and/or type II IFN production, and/or of TNF-α and/or IL1-β and/or IL-6 and/or RANTES and/or MCP-1. This application of the inventive dsRNA is especially useful in the treatment of infectious diseases, e.g. by viruses (such as Herpesvirus, Papillomavirus), bacteria, parasites or fungi, or in the treatment of cancer.

The improved immunostimulatory effects of the double-stranded ribonucleic acids of the present invention as well as their compositions as defined herein are especially useful in therapeutic or prophylactic vaccine preparations directed to a certain disease. Thus, the dsRNA and compositions of the invention may also be used as an "RNA adjuvant" in vaccine preparations (or administered in a distinct preparation together with the vaccine or antigen, respectively, or sequentially). Accordingly, preferred pharmaceutical compositions of this aspect further comprise an antigen of interest to generate a specific immune response (antibody response or cellular immune response, i.e. CD8+ T cell response and/or NK cell response) against the antigen, optionally together with a further adjuvant known in the art. Simultaneous or sequential administration of the antigen/vaccine and the immunostimulatory dsRNA or compositions of the present invention should improve the immune response against the antigen of the vaccine by generating a protective CD8+ T cell response and/or NK cell response to soluble proteins (antigens), triggering DC, macrophage and/or monocyte activation and induction of type I and/or type II IFN production, and/or of TNF-α and/or IL1-β and/or IL-6 and/or RANTES and/or MCP-1.

Accordingly, the present invention relates also to methods for induction of cytokines, in particular induction of type I and/or type II IFN production, and/or of TNF-α and/or IL1-δ and/or IL-6 and/or RANTES and/or MCP-1 in immune cells, especially DCs, macrophages or monocytes, in vitro or in vivo, in particular when present in a subject, preferably a mammal, more preferably a human, especially when in need for such induction of such cytokines.

The double-stranded ribonucleic acids or pharmaceutical compositions as disclosed herein can also be combined with one or more further therapeutic agents known in the art such as immunomodulatory drugs, e.g. immunostimulatory drugs, anti-cancer or anti-tumor, respectively, drugs and/or drugs for immunotherapy through activation of innate immunity or induction of apoptosis in cancer or tumor cells.

As outlined above, the dsRNAs of the invention and their pharmaceutical compositions are not only useful as immunomodulatory, in particular immunostimulatory agents, activating the innate immunity effectors and cells such as natural killer cells, lymphocytes, dendritic cells, macrophages and monocytes (either as an immunomodulatory, especially immunostimulatory, or drug for immunotherapy through activation of innate immunity or induction of apoptosis in cancer or tumor cells, or as an RNA therapeutic and/or prophylactic vaccine), but also show a pro-apoptotic activity, especially on cancer or tumor cells. Thus, the invention also comprises the use of dsRNAs as well as pharmaceutical compositions thereof as described herein for inducing apoptosis in a cell, preferably a tumor or cancer cell. In corresponding methods, the dsRNA according to the invention, or suitable composition thereof as outlined above, in particular in form of a pharmaceutical composition is suitably administered in an effective amount to a cell and/or tissue in vitro or in vivo, preferably to an organism in need of such apoptotic treatment, particularly preferred to a human patient suffering from a tumor or a cancer disease, or in the remission phase after having suffered from a tumor or cancer disease.

According to the present invention, the term "tumor" includes benign and malignant tumors. Malignant tumors may be regarded as a synonym of "cancer".

In preferred embodiments, the dsRNA or pharmaceutical composition used as an anti-tumor or anti-cancer drug is employed in combination with one or more further preventive or therapeutic anti-tumor or anti-cancer regimens such as, for example, radiotherapy, anti-cancer or anti-tumor drugs, preferably chemotherapeutic drugs and/or biosimilars (e.g. monoclonal antibodies, nucleic acid compositions such as oligonucleotides or polynucleotides, Toll-like receptor antagonists, and antibody-drug conjugates (ADC)), and/or surgery. Such further therapeutic and/or preventive anti-tumor or anti-cancer regimen can be applied to the patient, preferably a human patient, simultaneously or sequentially with the administration of a dsRNA or compositions thereof according to the invention. "Preventive" treatments as described herein are also meant for preventing and/or treating remissions of tumors and/or cancer in subjects who had undergone therapeutic anti-cancer or anti-tumor regimens previously.

Chemotherapeutic anti-tumor and/or anti-cancer drugs useful in this context are preferably selected from cytostatics such as alkylating agents, platinum complexes, intercalating agents, antibiotics, mitosis inhibitors, taxanes, topoisomerase inhibitors, anti-metabolites or other classes of known cytostatics.

Preferred examples of alkylating agents include nitrogen-lost derivatives such as cyclophosphamide, ifosfamide, trofosfamide, melphalan, chloroambucile and estramustine; alkyl sulfonates such as busalfane and treosulfane; nitroso urea compounds such as carmustine, lomustine, nimustine and streptozocine; procarbazine, dacarbazine, temozolomide, and thiotepa.

Examples of platinum compounds useful in anti-tumor therapies according to the invention include cisplatin, carboplatin, oxaliplatin and satraplatin.

Suitable intercalating agents for use in the present invention include mitoxantrone, amsacrine, and anthracyclines such as docorubicine, daunorubicine, epirubicine and idarubicine.

Suitable antibiotics as additional chemotherapeutic drugs for anti-tumor therapy include bleomycine, actinomycine D, and mitomycine.

Preferred mitosis inhibitors for use in the present invention are typically selected from vinorelbine, vincristine, vinblastine, and vindesine.

Suitable taxanes in this context of the invention are preferably selected from paclitaxel, docetaxel and cabazitaxel.

Topoisomerase inhibitors fur use in the invention as additional anti-tumor drugs are selected from topoisomerase I inhibitors such as comptothecine, topotecan and irinotecan, and topoisomerase II inhibitors such as etoposide and teniposide.

Preferred anti-metabolites in this context of the invention include folic acid antagonists such as methotrexate and pemetrexed, pyrimidine analogues, preferably azacitidine, decitabine, 5-fluoro uracil, capecitabine, doxifluridine, cytarabine and/or gemcitabine, as well as purine analogues such as 6-thio guanine, pentostatine, azathioprine, 6-mercaptopurine, fludarabine and cladribine.

Further preferred cytostatics for use as additional tumor therapeutics according to the invention include L-asparaginase; tyrosine kinase inhibitors such as imatinib, dasatinib and nilotinib; hydroxycarbamide; mitotane; amatoxins; altretamine; and aromatase inhibitors such as anastrozole, exemestane and letrozole.

Further especially preferred anti-tumor and/or anti-cancer drugs useful in the context of the present invention include other pro-apoptotic agents, particularly preferred so-called immune checkpoint inhibitors such as antibodies directed to PD-1, PD-1L or CTLA-4. Specific examples of such immune checkpoint inhibitors include Ipilimumab and Nivolumab.

Yet further especially preferred anti-tumor and/or anti-cancer drugs useful in the context of the present invention include biosimilars such as humanized monoclonal antibodies targeting cancer cells and/or cells implicated in cancer cell growth, particularly preferred so-called anti-VEGF antibodies such as Bevacizumab (Avastin®) or anti-tumor specific antigen antibodies such as anti-HER2 neu (Trastuzumab, Herceptin®).

Still further especially preferred anti-tumor and/or anti-cancer drugs useful in the context of the present invention include known nucleic acid compositions such as oligonucleotide or polynucleotide compositions used in therapeutic indications such as small interfering RNA (siRNA) compositions, microRNA mimics compositions, DNA compositions, RNA compositions used also, but not limited to this use, as immunoadjuvants for therapeutic or prophylactic vaccination.

Further especially preferred anti-tumor and/or anti-cancer drugs useful in the context of the present invention include further known Toll-like receptor (TLR) agonists selected but not limited to the group of TLR1 to TLR10 such as Imiquimod, Resiquimod, poly(I:C), BCG, and CpG oligonucleotides.

Further especially preferred anti-tumor and/or anti-cancer drugs useful in the context of the present invention include antibody-drug conjugates (ADC).

The ribonucleic acids of the present invention are particularly useful in the prevention and/or treatment of diseases, including infectious diseases caused by infectious agents such as bacteria, viruses, parasites and fungi, and tumors or cancers.

The present invention also provides a method for the prevention and/or treatment of a disease as mentioned above, preferably a viral infection or a cancer or tumor disease, comprising administering an effective amount of the pharmaceutical composition of the invention to a preferably mammalian, particularly human, subject in need of such treatment.

Administration routes for pharmaceutical compositions as defined herein, and in the context of medical treatments which may be prophylactic or therapeutic, include subcutaneous, intra-dermal, intra-muscular, intra-peritoneal, intrathecal, intra-ocular and/or intra-venous injection in a single or repeated dose, optionally combined with an antigen and/or immunogenic peptide, further optionally combined with another adjuvant that may be present in a depot form (such as an Aluminium salt), or combined with a further activator of innate immunity such as agonists of toll-like receptor 1 to 10 (TLR1 to TLR10). Preferred examples of further TL3 agonists are disclosed in, e.g. WO-A-2013/064584 and Naumann et al., supra.

It is also contemplated to provide the dsRNAs or compositions thereof and antigens and/or additional adjuvants and/or additional active agents (such as additional agents for anti-tumor or anti-cancer therapy as outlined above) in separate same or different formulations and to administer these formulations to the patient separately, e.g. by injection such as intra muscular injection, at the same of different locations, e.g. the inventive dsRNA or composition thereof at one location, and the antigen and/or additional adjuvant and/or additional active agent at a different location.

In general, a suitable dose of dsRNAs of the invention will be in the range of 0.01 to 500 µg per kilogram body weight of the subject per day, typically about 1 µg per kg to about 500 µg per kg, preferably about 1 µg per kg to about 250 µg per kg such as about 50 µg per kg to about 100 µg per kg, or about 1 µg per kg to about 50 µg per kilogram body weight of the subject to be treated. Alternatively, a suitable dose of dsRNAs of the invention will be in the range of 0.1 to 10 mg per square meter body surface of the subject per day, typically about 0.5 mg per square meter to about 5 mg per square meter, preferably about 1 mg per square meter to about 2.5 mg per square meter body surface of the subject to be treated. The pharmaceutical composition may be administered once per day, or the dsRNA(s) may be administered as two, three, four, five, six or more sub-doses at appropriate intervals per day. The skilled person understands that in case of multiple doses per day, the individual dose must be adapted to reach the selected daily dose.

The dosage unit can also be adapted for delivery over more than one day, e.g. using conventional sustained release formulations known in the art, which provide a sustained release of the dsRNA(s) over the selected period such as over two or more days. In such embodiments, the dosage unit typically contains a corresponding multiple of the chosen daily dose of the dsRNA(s).

The present invention also relates to a cell or non-human organism being transfected, transduced or transformed with the double-stranded RNA molecules or compositions as defined herein.

Figure 1:
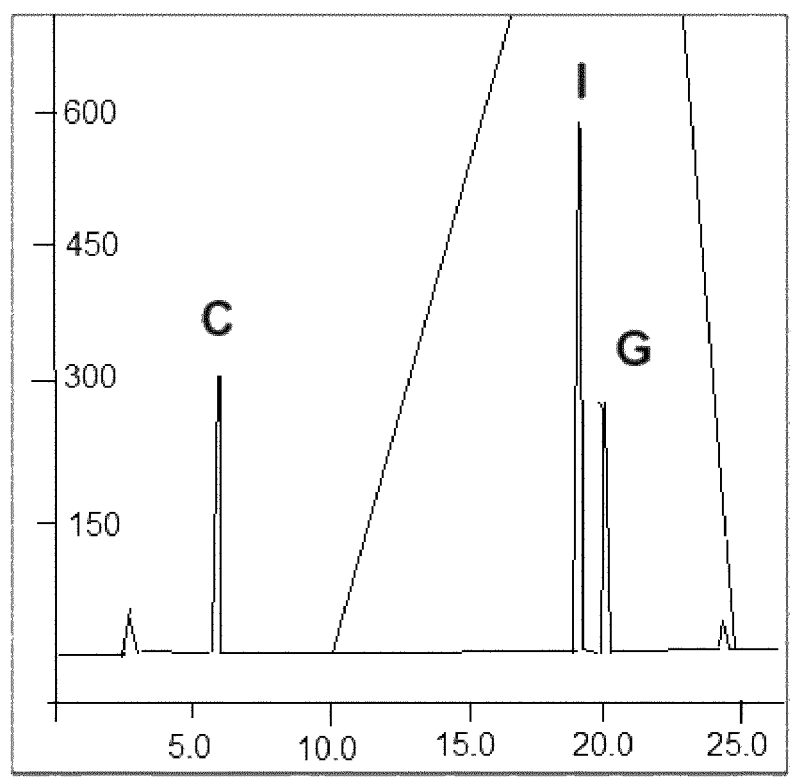
FIG. 1: HPLC elution profile of an exemplary composition of dsRNAs according to the invention (RGIC 100.1) after complete digestion with phosphodiesterase. Elution peaks of the resulting cytosine, inosine and guanosine nucleotides are indicated.

The resulting $B_{max}$ and $K_D$ values for the three dsRNA compositions are as follows: RGIC 100.1: $B_{max}$=2.886, $K_D$=0.072 µg/ml; RGIC 100.2: $B_{max}$=4.374, $K_D$=0.030 µg/ml; RGIC 100.3: $B_{max}$=2.293, $K_D$=0.179 µg/ml.

FIG. 14: dsRNA of the invention induces apoptosis in HeLa cells. (A) Assessment of apoptosis of HeLa cells after incubation with RGIC 100.2 at the indicated concentrations. Asterisks indicate a statistically significant difference (student's t-test p<0.05). (B) to (E) Flow cytometry data of HeLa cells incubated with 1 µg/ml RGIC 100.2 (B), 5 µg/ml RGIC 100.2 (C), cells incubated with transfection reagent alone (D) or cells incubated without any reagents (E); FL1 channel, Annexin V. FL2 channel, propidium iodide. Increased apoptosis of HeLA cells incubated with 1 µg/ml and 5 µg/ml RGIC 100.2 in comparison to HeLa cells incubated with transfection reagent (tfx) or culture medium only (cc) is detected.

FIG. 15: dsRNA of the invention does not induce apoptosis in immune cells. (A) Assessment of apoptosis of JAWS II DCs and RAW 264.7 macrophages after incubation with RGIC 100.2 at the indicated concentration in comparison to cells without treatment with RGIC 1002. (B) and (C) Flow cytometry data of JAWS II DCs incubated with 1 µg/ml RGIC 100.2 (B) or incubated with cell culture medium only (C). (D) and (E) Flow cytometry data of RAW 264.7 macrophages incubated with 1 µg/ml RGIC 100.2 (D) or incubated with cell culture medium only (E); FL1 channel, Annexin V. FL2 channel, propidium iodide. No statistical relevant difference between the immune cells incubated with dsRNA of the invention and cells incubated with culture medium only (cc) is detected.

FIG. 16: dsRNA of the invention does not induce apoptosis in non-immune cells. (A) Assessment of apoptosis of 2H-11 endothelial cells and HUVECs after incubation with RGIC 100.2 at the indicated concentration in comparison to cells without treatment with RGIC 1002. (B) and (C) Flow cytometry data of 2H-11 endothelial cells incubated with 1 µg/ml RGIC 100.2 (B) or incubated with transfection reagent only (C). (D) and (E) Flow cytometry data of HUVECs incubated with 1 µg/ml RGIC 100.2 (D) or incubated with transfection reagent only (E); FL1 channel, Annexin V. FL2 channel, propidium iodide. No statistical relevant difference between the non-immune cells incubated with dsRNA of the invention and cells incubated with culture medium only (cc) is detected.

DETAILED DESCRIPTION OF THE INVENTION

The following non-limiting examples further illustrate the present invention.

EXAMPLES

Example 1: Production of dsRNA Compositions According to the Invention dsRNA compositions from two different polyC ssRNA templates ($C_{50}$ and $C_{100}$, respectively) were produced essentially as described in WO-A-2009/150156 using corresponding mixtures of rITP and rGTP.

Briefly, the reaction mix of 50 µl contained template $C_{50}$ or $C_{100}$ template at 1 µg/µl in 50 mM HEPES pH 7.6, 5 mM $MnCl_2$, 1 mM DTT, 7 µM Sapovirus RdRp and the appropriate mix of rITP and rGTP.

Reactions were incubated at 30° C. for 2 h.

In this way, three different compositions of dsRNAs having a length of 100 bp (compositions RGIC 100.1, RGIC 100.2, RGIC 100.3) and four different compositions of dsRNAs having a length of 50 bp (RGIC 50.1, RGIC50.2, RGIC 50.3, RGIC 50.4) were generated.

Example 2: Characterization of dsRNA Compositions According to the Invention The dsRNA compositions produced according to Example 1 were subjected to base composition analysis (BCA). Each composition was digested by phosphodiesterase and the reaction products analyzed by HPLC. An exemplary elution profile is shown for composition RGIC 100.1 in FIG. 1. The area under the curve of the released G, C, and I nucleotides was measured and the proportion of each nucleoside in the reaction assessed. For comparison, a poly(G:C) construct (($G:C)_{100}$) was analyzed as well.

The BCA results are shown in below Table 1:

TABLE 1

Results of base composition analysis

| | | Composition [mol-%] | | |
|---|---|---|---|---|
| Construct | Length [bp] | G | C | I |
| RGIC 100.1 | 100 | 11 | 50 | 39 |
| RGIC 100.2 | 100 | 22 | 50 | 28 |
| RGIC 100.3 | 100 | 34 | 50 | 16 |
| RGIC 50.1 | 50 | 15 | 50 | 35 |
| RGIC 50.2 | 50 | 21 | 50 | 29 |
| RGIC 50.3 | 50 | 33 | 50 | 17 |
| RGIC 50.4 | 50 | 44 | 50 | 6 |
| $(G:C)_{100}$ | 100 | 50 | 50 | 0 |

Figure 2:
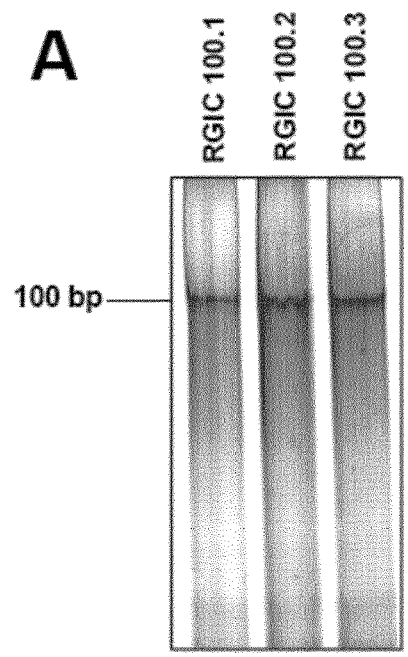
FIG. 2: Size analysis of different exemplary inventive compositions of dsRNAs according to the invention. (A) Three different compositions containing dsRNAs of 100 bp but different base composition (RGIC 100.1, RGIC 100.2, RGIC 100.3) were analyzed by 12% native polyacrylamide gel electrophoresis (PAGE). Samples were stained with GelRed and visualized by UVtransillumination. (B) Four different compositions containing dsRNAs of 50 bp but different base composition (RGIC 50.1, RGIC 50.2, RGIC 50.3, RGIC 50.4) were analyzed by 12% native polyacrylamide gel electrophoresis (PAGE). Samples were stained with GelRed and visualized by UV transillumination.
Figure 2:
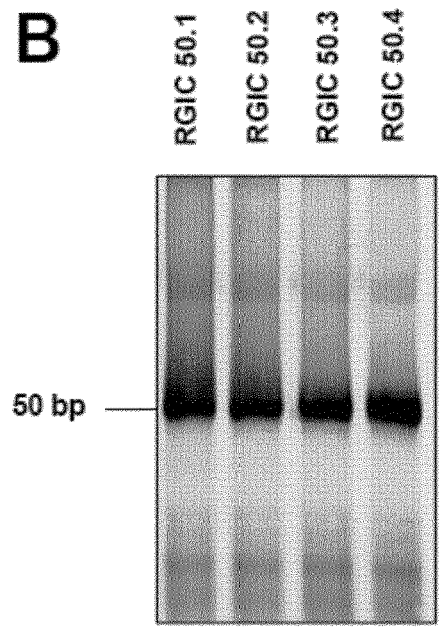

Analysis of the length and integrity of the dsRNAs in the inventive compositions was performed on 12% native PAGE. DNA marker (Fermentas, Germany) was used to illustrate molecular size distribution and RNA staining was achieved by using GelRed (Biotium, Hayqard, Calif., USA). The results are shown in FIG. 2A and FIG. 2B demonstrating that each of the inventive dsRNA compositions contains dsRNAs having a defined length of 100 bp or 50 bp, respectively.

Example 3: Activation of JAWS II Dendritic Cells and RAW 264.7 Macrophages by dsRNA Compositions According to the Invention JAWS II and RAW 264.7 cell lines were obtained from American Type Culture Collection (ATCC; Manassas, Va., USA). JAWS II is an immortalized immature myeloid DC line derived from C57BL/6 mice, which displays a similar phenotypic profile as resting bone-marrow-derived DCs (BMDCs) (Jiang et al. (2008) Infection and Immunity 76 (6), 2392-2401). RAW 264.7 is a mouse leukemic monocyte/macrophage cell line which was established from the ascites of a tumor induced in a male mouse by intraperitoneal injection of Abelson Mouse Leukaemia Virus (A-MuLV).

Cells were plated in round-bottomed 96-well plates at $5 \times 10^4$ cells/well in DMEM supplemented with 10% fetal calf serum (FCS) and 1% penicillin/streptomycin (100 U/ml). Cells were incubated with the dsRNA compositions of Example 1 at different concentrations as indicated in FIGS. 3 to 12. In the experiment according to FIG. 3, a $(G:C)_{100}$ construct (RGC 100) at 50 µg/ml was used as a comparative example. In the experiments according to FIGS. 4, 7 and 8, poly(I:C) at 10 µg/ml (FIGS. 4 and 8) or at 50 µg/ml (FIG. 7) was used as a comparative example. In the experiment according to FIG. 5 the dsRNA composition RGIC 100.2 was used at the indicated concentrations with or without pre-incubation of JAWS II DCs with chloroquine (Invivogen, USA) at a concentration of 100 µM. The same experiment was carried out on RAW 264.7 macrophages (FIG. 10) and on JAWS II DCs (FIG. 11) using dsRNA composition RGIC 50.2 After 16 h, supernatants were collected and the concentration of IL-6 (in experiments using JAWS II DCs) or TNF-α (in experiments using RAW 264.7 macrophages) was determined by ELISA using the ELISArray kit (Qiagen, Hilden, Germany) following the respective manufacturer's instructions.

Figure 3:
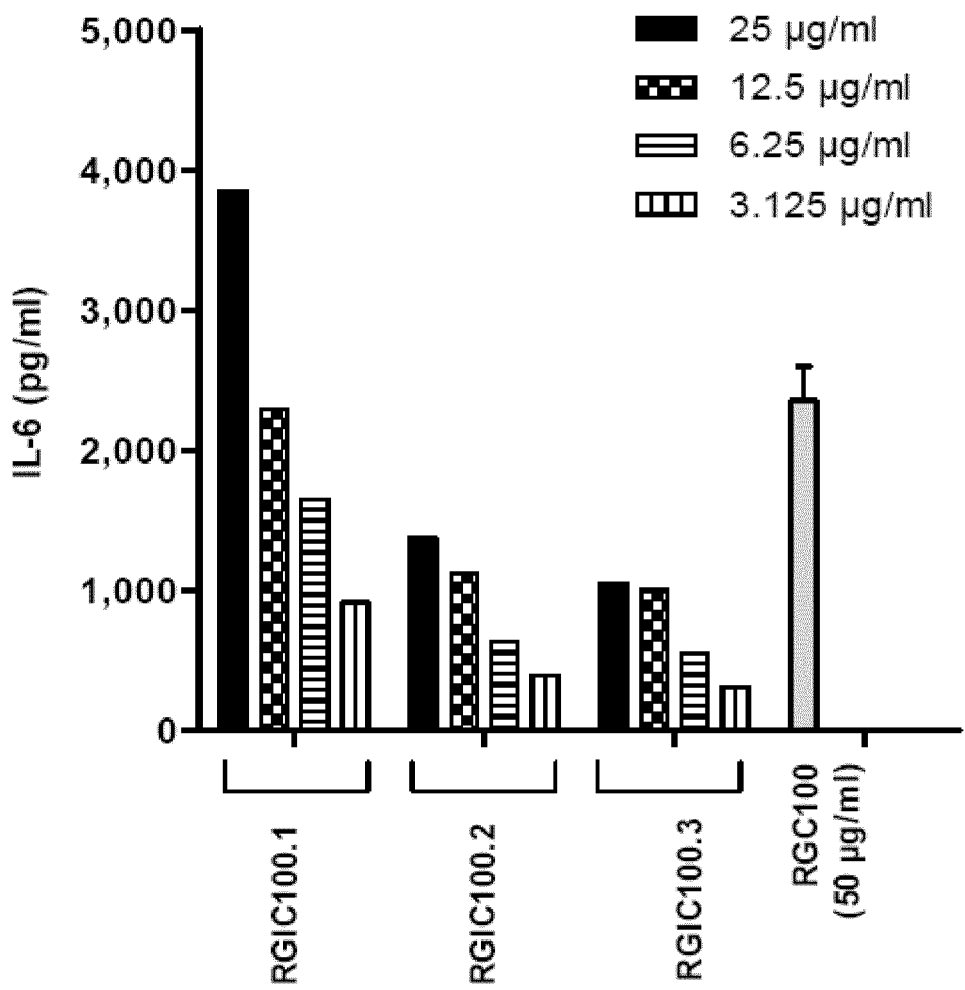
FIG. 3: Dose-dependent and inosine content-dependent activation of JAWS II DCs by 100 bp dsRNA compositions (RGIC 100.1, RGIC 100.2, RGIC 100.3) of the invention having different base compositions. Secretion of IL-6 by JAWS II DCs was measured in the culture supernatant. Values shown are the measured values minus the value of a negative control (medium without dsRNA composition). As a further control, a poly(G:C)$_{100}$ dsRNA (RGC 100) containing no inosine residues was used at a concentration of 50 µg/ml.
Figure 4:
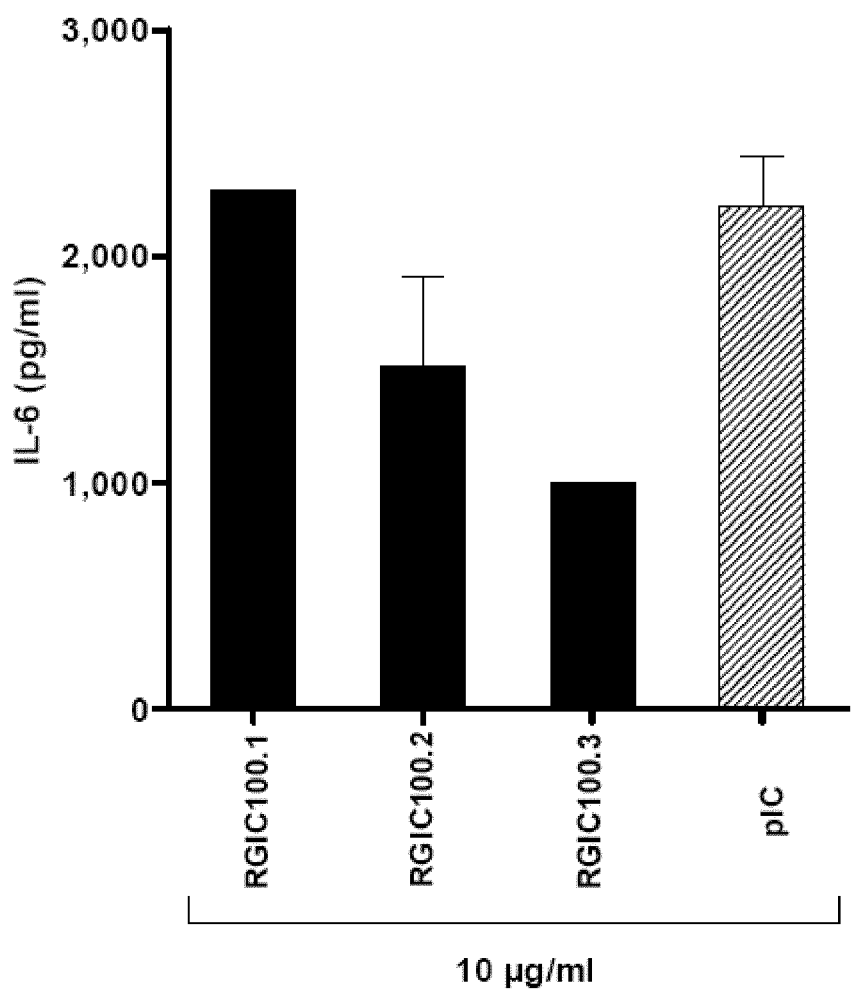
FIG. 4 Activation of JAWS II DCs by 100 bp dsRNA compositions of the invention (RGIC 100.1, RGIC 100.2, RGIC 100.3) in comparison to poly(I:C). The concentration of all three compositions of the invention was 10 µg/ml. Secretion of IL-6 by JAWS II DCs was measured in the culture supernatant. Values shown are the measured values minus the value of a negative control (medium without dsRNA composition). As a further control, poly(I:C) was used at the same concentration as that of the dsRNA compositions of the invention.

FIGS. 3 and 4 show that the activation of JAWS II DCs by dsRNA compositions according to the invention depends on the inosine content in the dsRNAs: the higher the inosine content in the dsRNA compositions, the more the DCs are activated as measured by the secretion of IL-6. Furthermore, the DC activation exerted by dsRNA composition RGIC 100.1 is as high as or even higher than that of poly(I:C); see FIG. 4.

Figure 5:
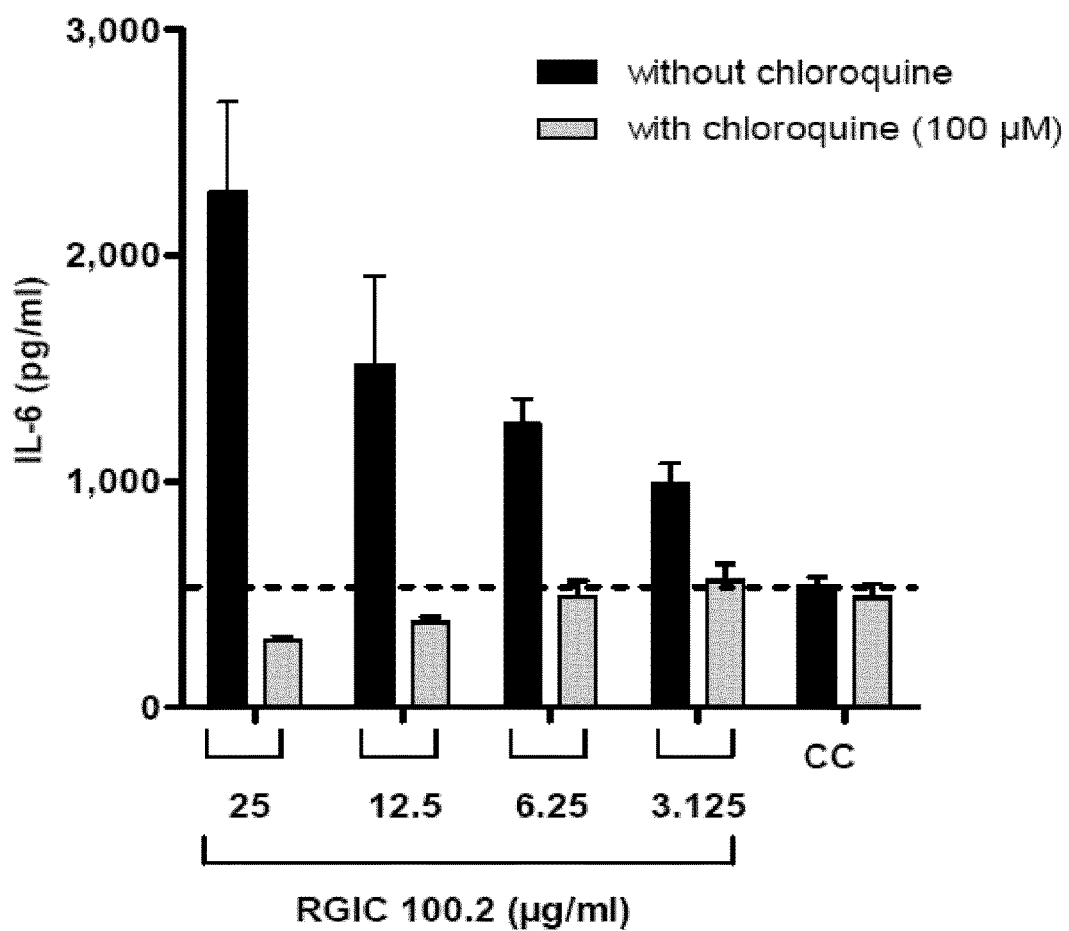
FIG. 5: Chloroquine inhibits the activation of JAWS II DCs by a 100 bp dsRNA composition of the invention (RGIC 100.2) demonstrating that the activation depends on endosomal acidification. Cells were first incubated with or without 100 µM chloroquine, then incubated with the dsRNA composition RGIC 100.2 at the indicated concentrations. Secretion of IL-6 by JAWS II DCs was measured in the culture supernatant. Values shown are the mean+/−SEM of two independent measurements. Supernatant of cells incubated in the absence of the dsRNA composition was used as negative control (CC).
Figure 10:
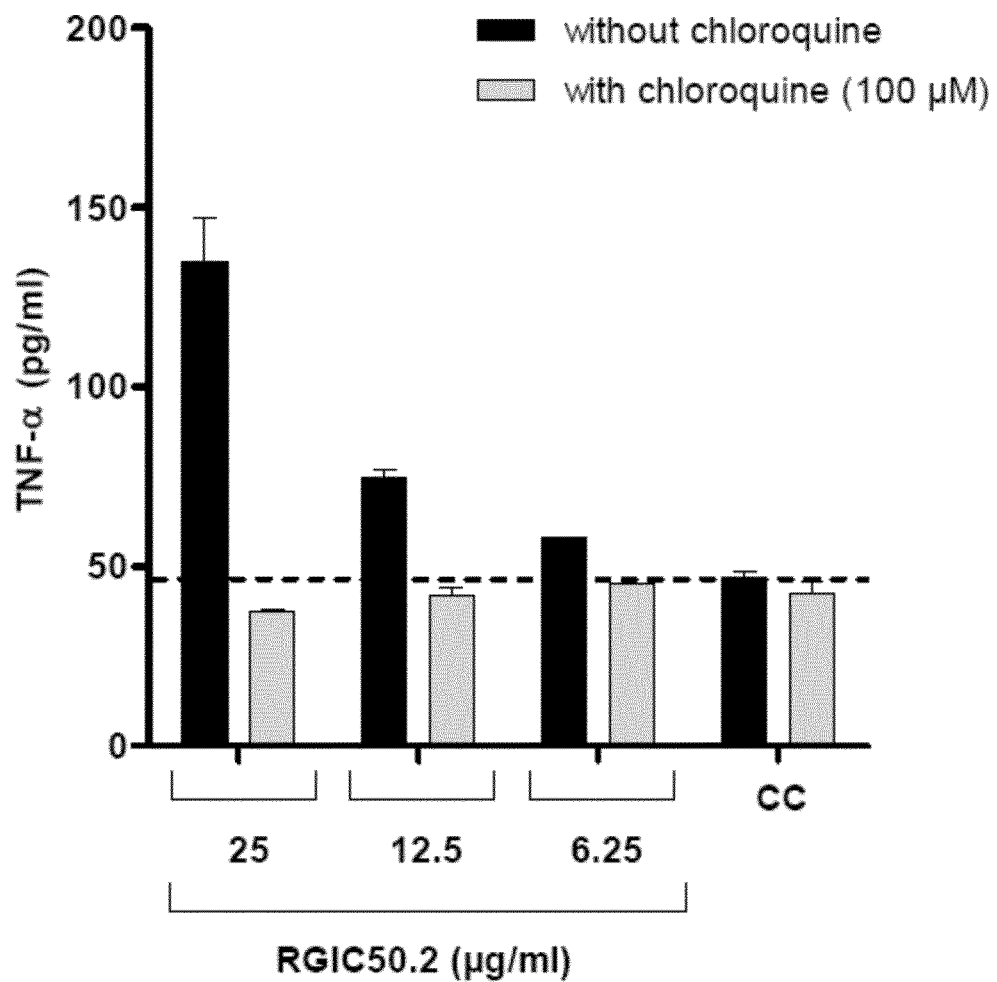
FIG. 10: Chloroquine inhibits the activation of RAW 264.7 macrophages by a 50 bp dsRNA composition of the invention (RGIC 50.2) demonstrating that the activation depends on endosomal acidification. Cells were first incubated with or without chloroquine (100 µM), then incubated with the dsRNA composition RGIC 50.2 at the indicated concentrations. Secretion of TNF-α by RAW 264.7 macrophages was measured in the culture supernatant. Values shown are the mean+/−SEM of two independent measurements. Supernatant of cells incubated in the absence of the dsRNA composition was used as negative control (CC).
Figure 11:
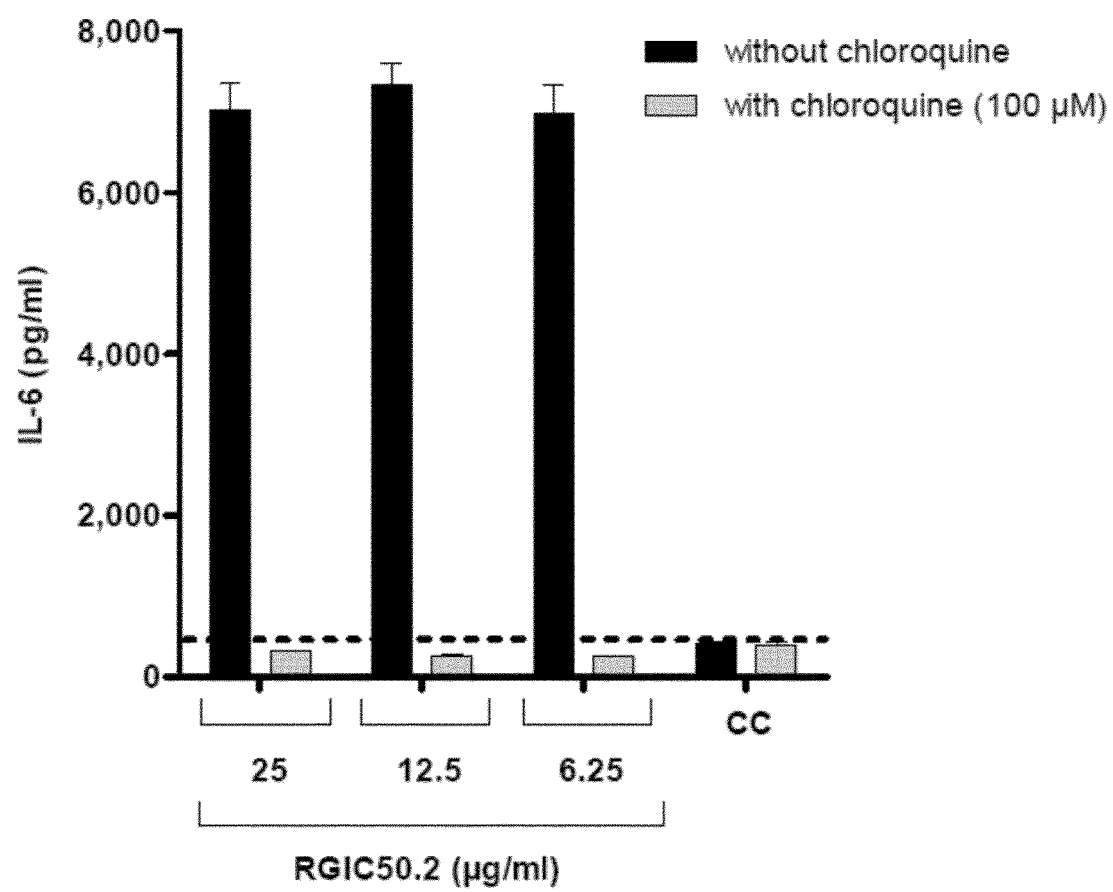
FIG. 11: Chloroquine inhibits the activation of JAWS II DCs by a 50 bp dsRNA composition of the invention (RGIC 50.2) demonstrating that the activation depends on endosomal acidification. Cells were first incubated with or without chloroquine (100 µM), then incubated with the dsRNA composition RGIC 50.2 at the indicated concentrations. Secretion of IL-6 by JAWS II DCs was measured in the culture supernatant. Values shown are the mean+/−SEM of two independent measurements. Supernatant of cells incubated in the absence of the dsRNA composition was used as negative control (CC).
Figure 12:
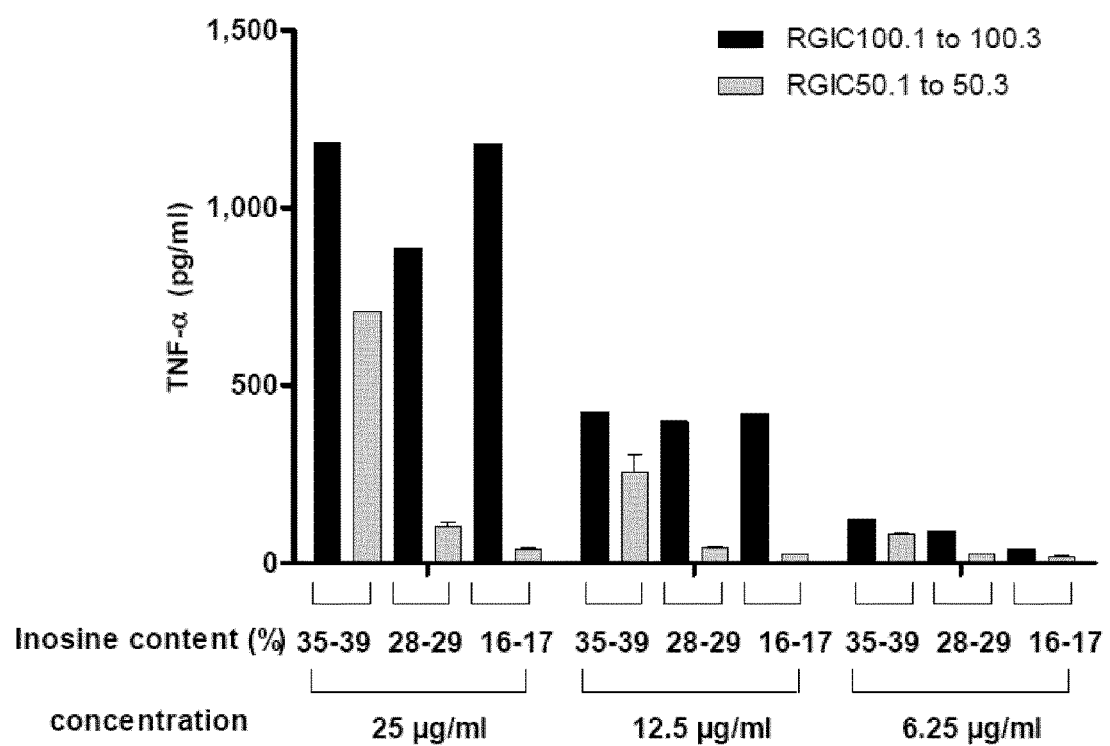
FIG. 12: Length and base composition of dsRNAs in the inventive compositions modulates the activation of RAW 264.7 macrophages. The macrophages were incubated with three different compositions of 50 bp dsRNAs (RGIC 50.1, RGIC 50.2, RGIC 50.3) and three different compositions of 100 bp dsRNAs (RGIC 100.1, RGIC 100.2, RGIC 100.3) at the indicated concentrations. The inosine content of the dsRNAs of the compositions is indicated as well. Values shown are the measured values minus the value of a negative control (medium without dsRNA composition).

FIGS. 5 and 11 show that the activation of JAWS II DCs by dsRNA compositions according to the invention is dependent on endosomal acidification: pre-incubation of the DCs with chloroquine hinders the activation of the DCs by dsRNA composition of the invention. FIG. 10 shows the same result for RAW 264.7 macrophages.

Figure 6:
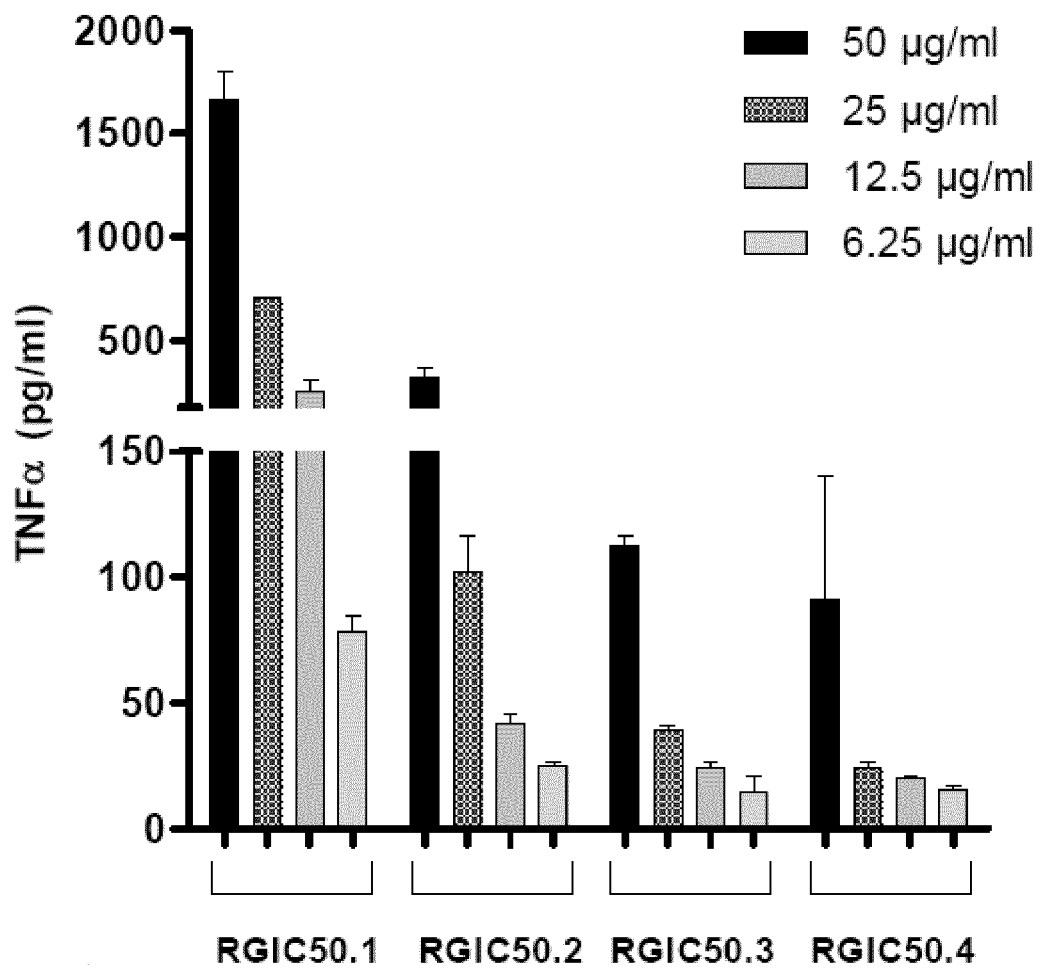
FIG. 6: Dose-dependent and inosine content-dependent activation of RAW 264.7 macrophages by 50 bp dsRNA compositions according to the invention (RGIC 50.1, RGIC 50.2, RGIC 50.3, RGIC 50.4). Secretion of TNF-α by RAW 264.7 macrophages was measured in the culture supernatant. Values shown are the measured values minus the value of a negative control (medium without dsRNA composition). As a further control, a poly(G:C)$_{100}$ dsRNA containing no inosine residues was used at a concentration of 50 µg/ml.
Figure 7:
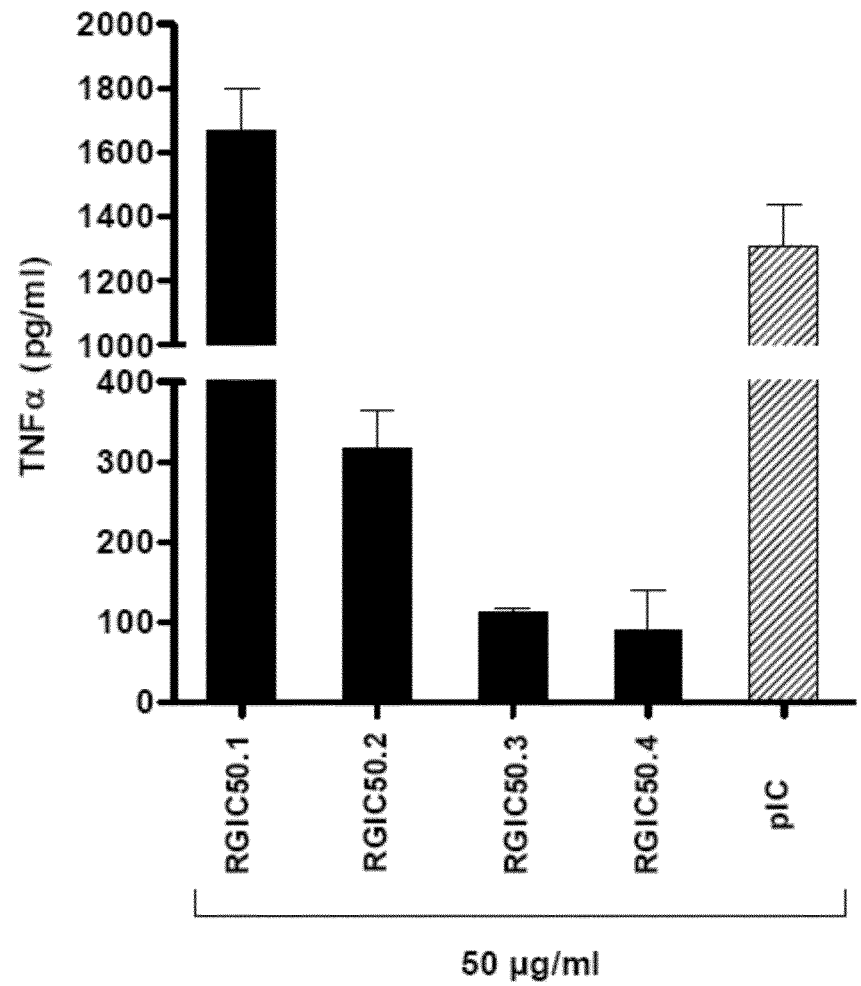
FIG. 7: Activation of RAW 264.7 macrophages by 50 bp dsRNA compositions of the invention (RGIC 50.1, RGIC 50.2, RGIC 50.3, RGIC 50.4) in comparison to poly(I:C). The concentration of all four compositions of the invention was 50 µg/ml. The secretion of TNF-α by RAW 264.7 macrophages was measured in the culture supernatant. Values shown are the measured values minus the value of a negative control (medium without dsRNA composition). As a further control, poly(I:C) was used at the same concentration as that of the dsRNA compositions of the invention.
Figure 8:
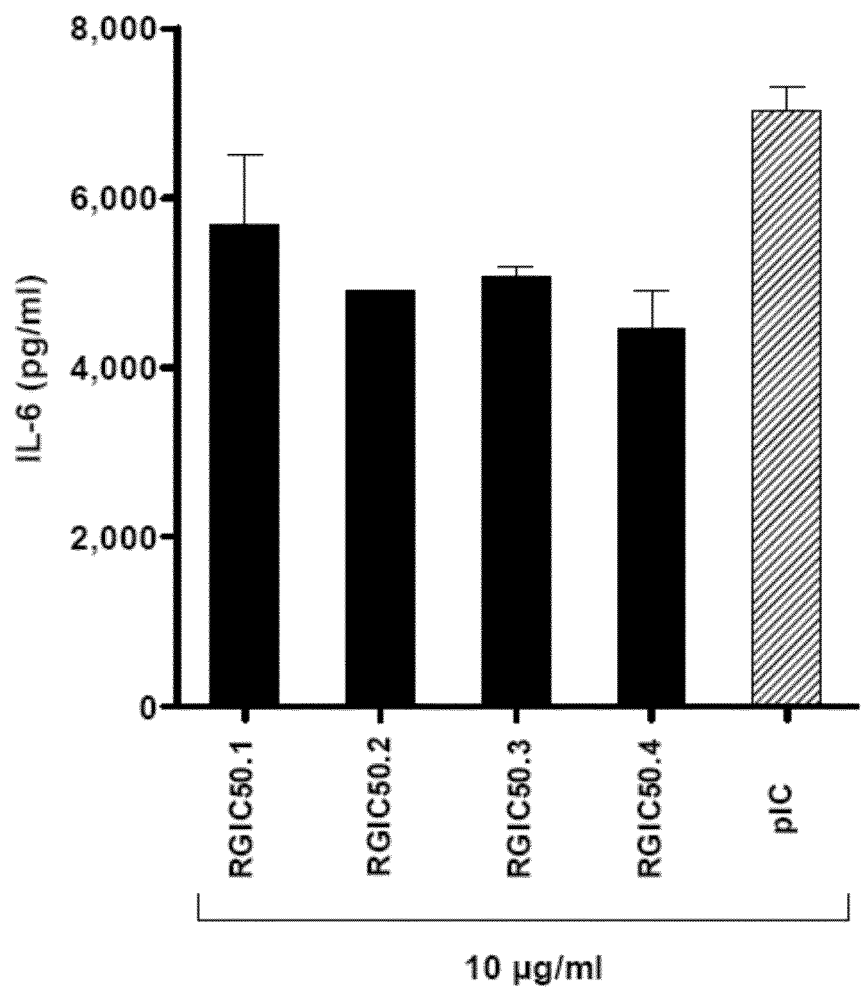
FIG. 8: Activation of JAWS II DCs by 50 bp dsRNA compositions of the invention (RGIC 50.1, RGIC 50.2, RGIC 50.3, RGIC 50.4) in comparison to poly(I:C). The concentration of all four compositions of the invention was 10 µg/ml. The secretion of IL-6 by JAWS II DCs was measured in the culture supernatant. Values shown are the measured values minus the value of a negative control (medium without dsRNA composition). As a further control, poly(I:C) was used at the same concentration as that of the dsRNA compositions of the invention.

FIGS. 6 and 7 show that the activation of RAW 264.7 macrophages by dsRNA compositions according to the invention depends on the inosine content in the dsRNAs: the higher the inosine content in the dsRNA compositions, the more the macrophages are activated as measured by the secretion of TNF-α. Furthermore, the macrophage activation exerted by dsRNA composition RGIC 50.1 is even higher than that of poly(I:C); see FIG. 7.

Example 4: Activation of Immune Cells by dsRNA Compositions of the Invention Depends on TLR3

In order to elucidate whether the presence of TLR3 is necessary for activation of immune cells by dsRNA compositions of the invention, gene silencing of TLR3 was performed using a siRNA (IBONI® siRNA, RiboxX GmbH, Radebeul, Germany) targeting TLR3 (5'-CTCGGCCT-TAATGAAATTGAA-3'; SEQ ID NO: 1). In comparison, a non-targeting IBONI® siRNA (RiboxX, Radebeul, Germany) was used. Therefore, RAW 264.7 cells were plated in round-bottomed 96-well plates at $5\times10^4$ cells/well and incubated at 37° C. (5% $CO_2$) for 16 h. Then, either IBONI® siRNA targeting TLR3 or control IBONI® siRNA was mixed with riboxxFECT transfection reagent (RiboxX, Radebeul, Germany) according to the manufacturer's instructions, and the respective mix was added to the wells at a siRNA concentration of 20 nM. At 6 h after transfection, dsRNA composition RGIC 50.1 was added at a concentration of 25 µg/ml, and the cells were incubated for further 16 h. Cell supernatants were used for measurement of TNF-α using the ELISArray kit (Qiagen, Hilden, Germany) according to the manufacturer's instructions.

Figure 9:
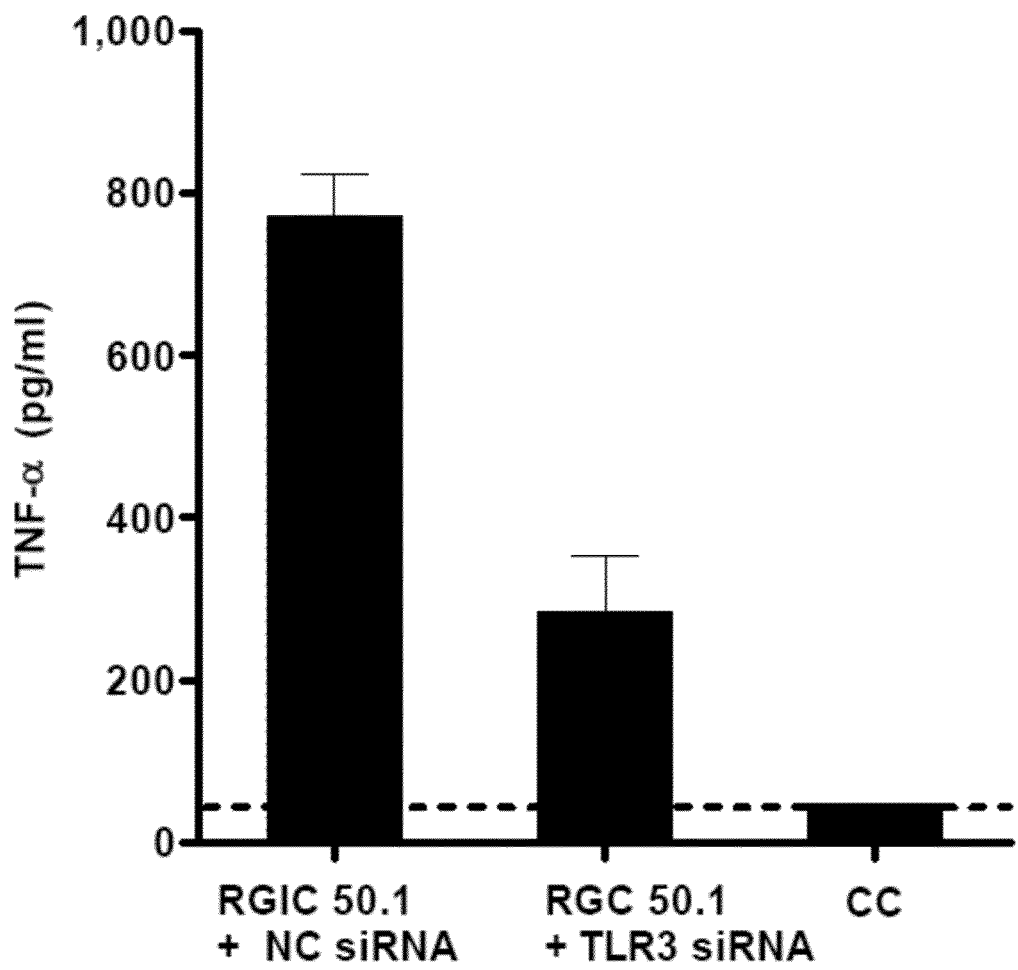
FIG. 9: Activation of RAW 264.7 macrophages by a 50 bp dsRNA composition of the invention (RGIC 50.1) is inhibited by a siRNA targeting TLR3. Cells were first incubated with an siRNA targeting TLR3 (TLR3 siRNA) or with a control siRNA (NC siRNA) not targeting TLR3, then incubated with a 50 bp dsRNA composition of the invention (RGIC 50.1) at 50 µg/ml. Secretion of TNF-α by RAW 264.7 macrophages was measured in the culture supernatant. Values shown are the mean+/−SEM of two independent measurements. CC: cell culture medium.

As shown in FIG. 9, the TNF-α concentration is strongly diminished in the supernatant of macrophages that were pre-transfected with the siRNA targeting TLR3 in comparison to cells that were pre-transfected with a control siRNA demonstrating that the activation of macrophages by dsRNA compositions depends on the expression of TLR3 in the immune cells.

Example 5: Binding Kinetics of dsRNA Composition According to the Invention to TLR3

HEK-Blue™ hTLR3 cells were obtained from InvivoGen (San Diego, Calif., USA). HEK-Blue hTLR3™ cells are designed for studying the stimulation of human TLR3 by monitoring the activation of NF-kB. HEK-Blue™ hTLR3 cells were generated by co-transfection of the hTLR3 gene and an optimized secreted embryonic alkaline phosphatase (SEAP) reporter gene placed under the control of an NF-kB and AP-1 inducible promoter into HEK293 cells. Stimulation with a TLR3 ligand activates NF-kB and AP-1 which induces the production of SEAP. Levels of SEAP in the cell supernatant can be readily determined by QUANTI-Blue™ (InvivoGen, San Diego, Calif., USA), a detection medium that turns purple/blue in the presence of alkaline phosphatase.

Figure 13A:
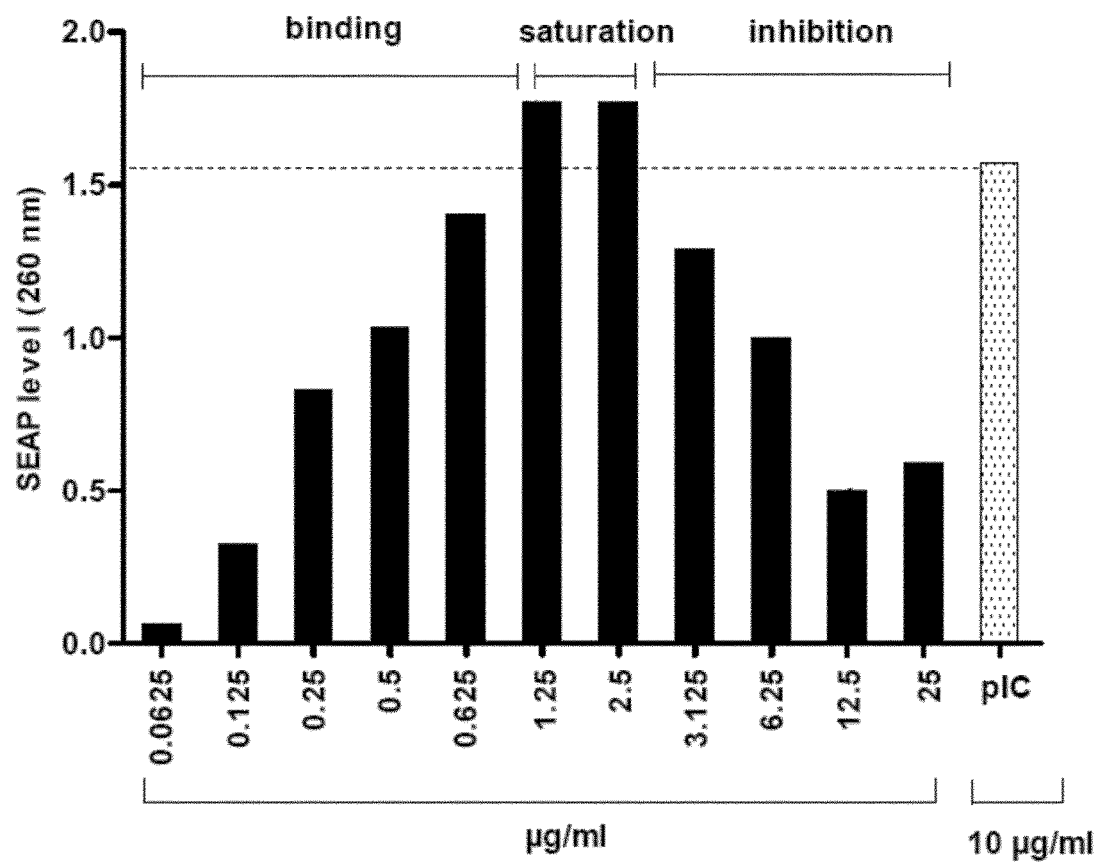
FIG. 13: dsRNA compositions of the invention having different base compositions (RGIC 100.1, RGIC 100.2, RGIC 100.3) display a strong activity to human TLR3 (hTLR3) as shown by the activation of HEK-Blue hTLR3 cells (Invivogen, USA). Activation of HEK-blue hTLR3 cells was measured at the indicated concentrations of RGIC 100.1 (A), RGIC 100.2 (B), or RGIC 100.3 (C) by measurement of SEAP levels at 260 nm. Values shown are the measured values minus the value of a negative control (medium without dsRNA composition). As a further control, poly(I:C) was used at a concentration of 10 µg/ml. (D) shows the binding curves for all three compositions in one graph.
Figure 13B:
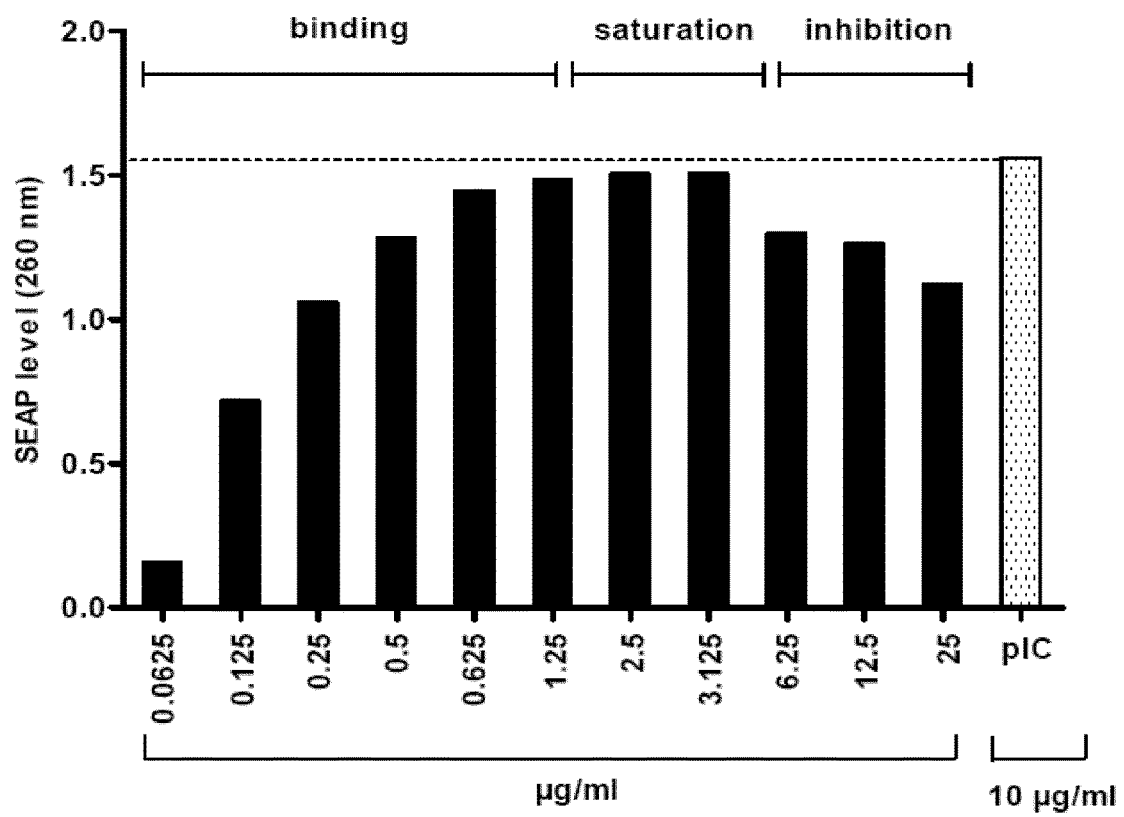
Figure 13C:
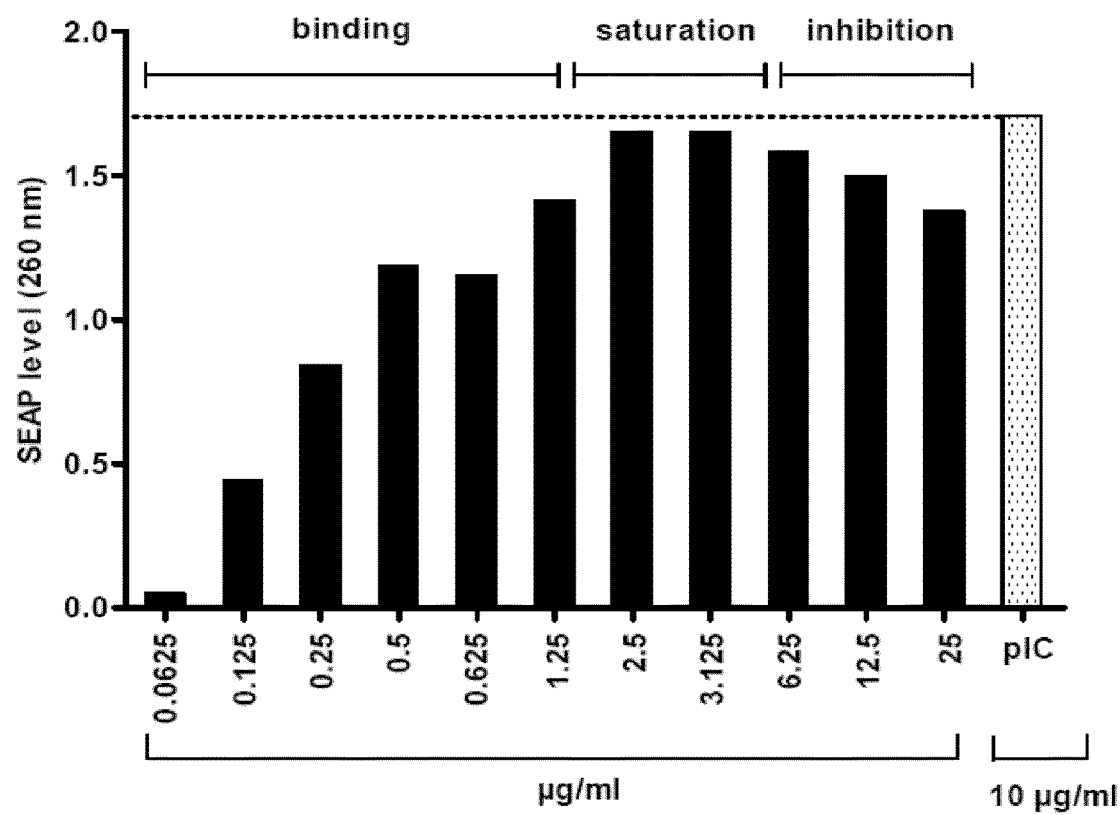
Figure 13D:
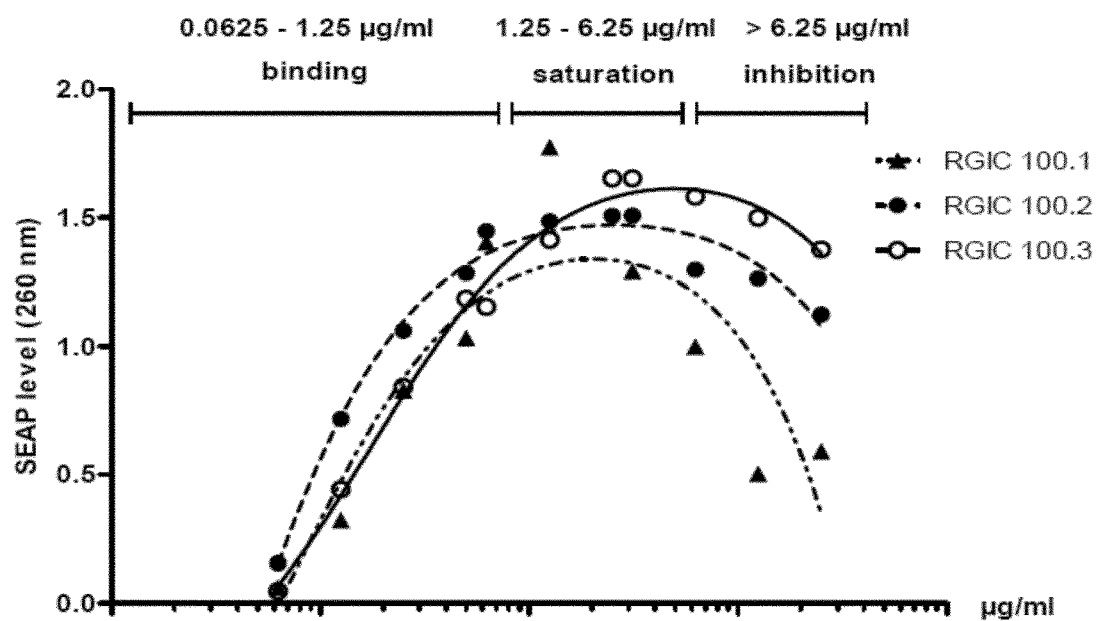
Figure 14A:
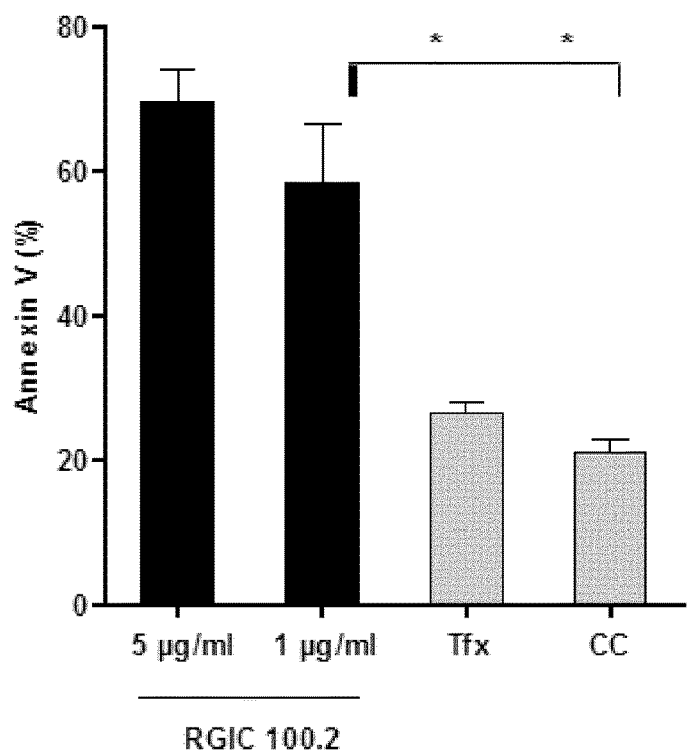
Figure 14B:
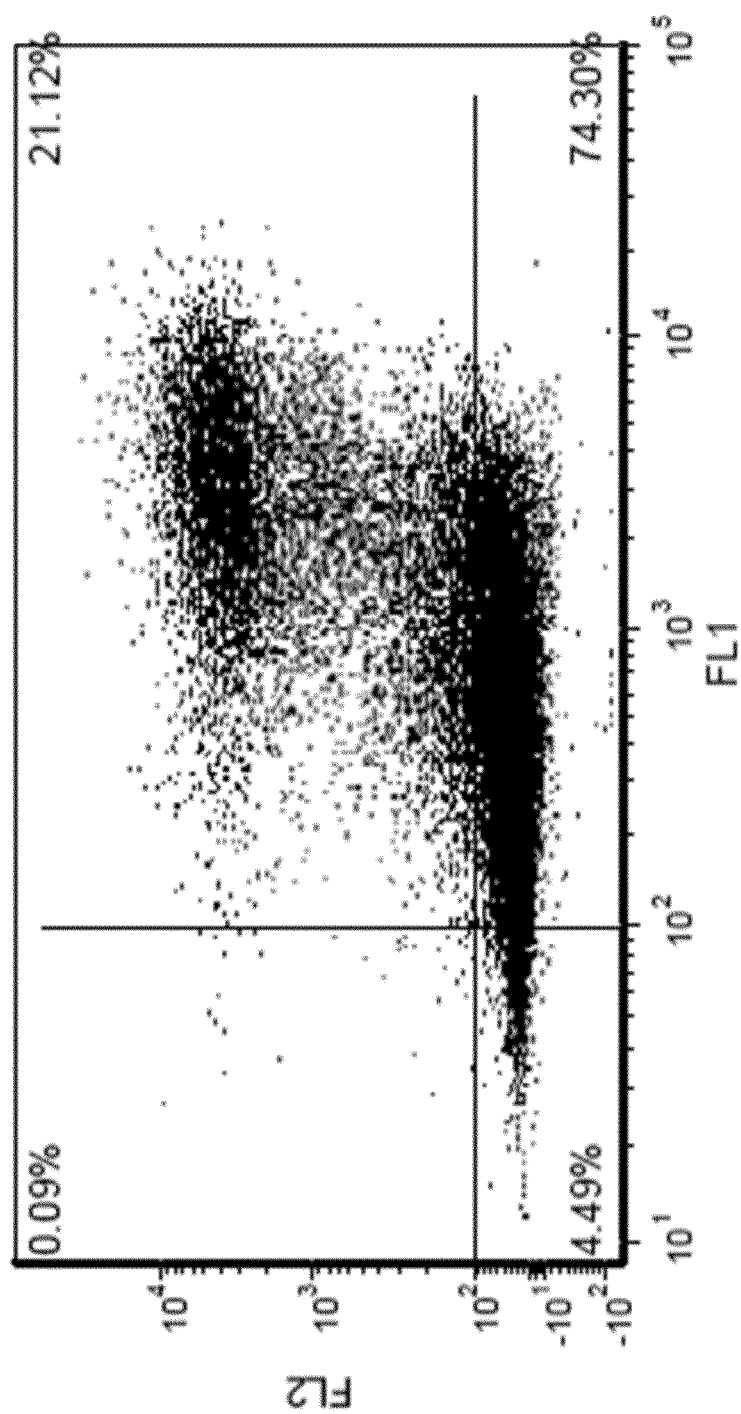
Figure 14C:
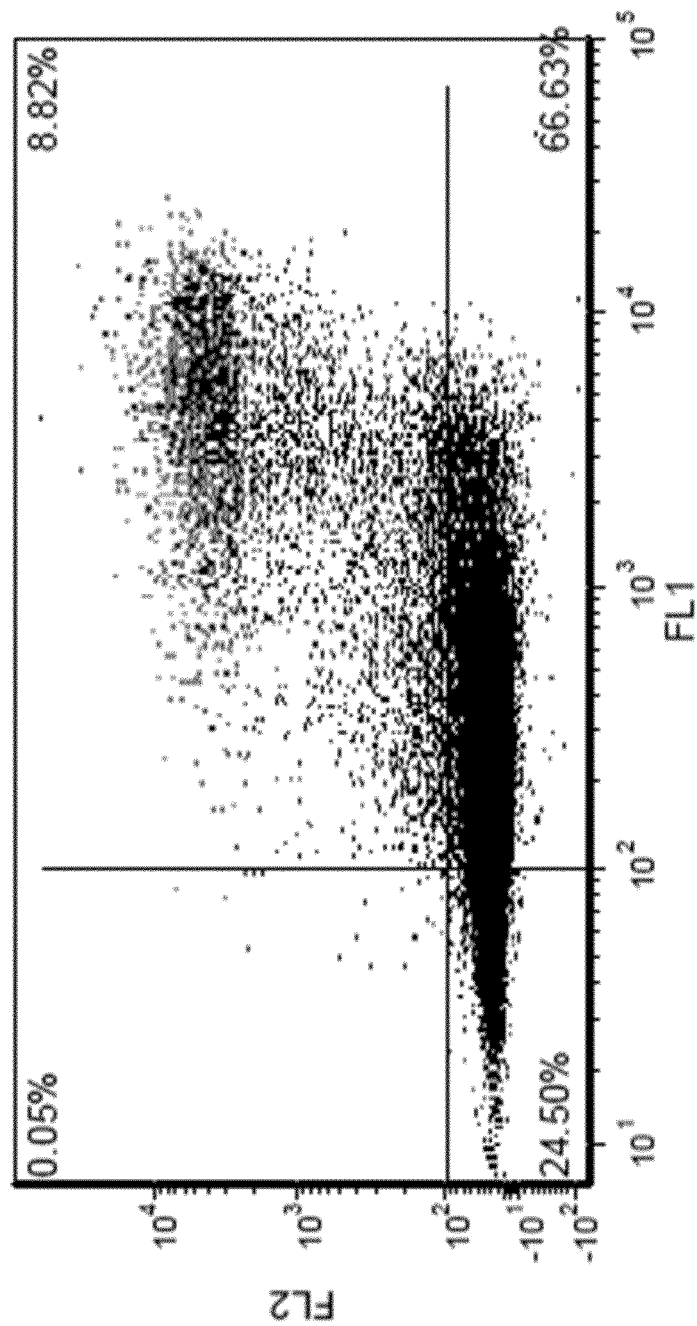
Figure 14D:
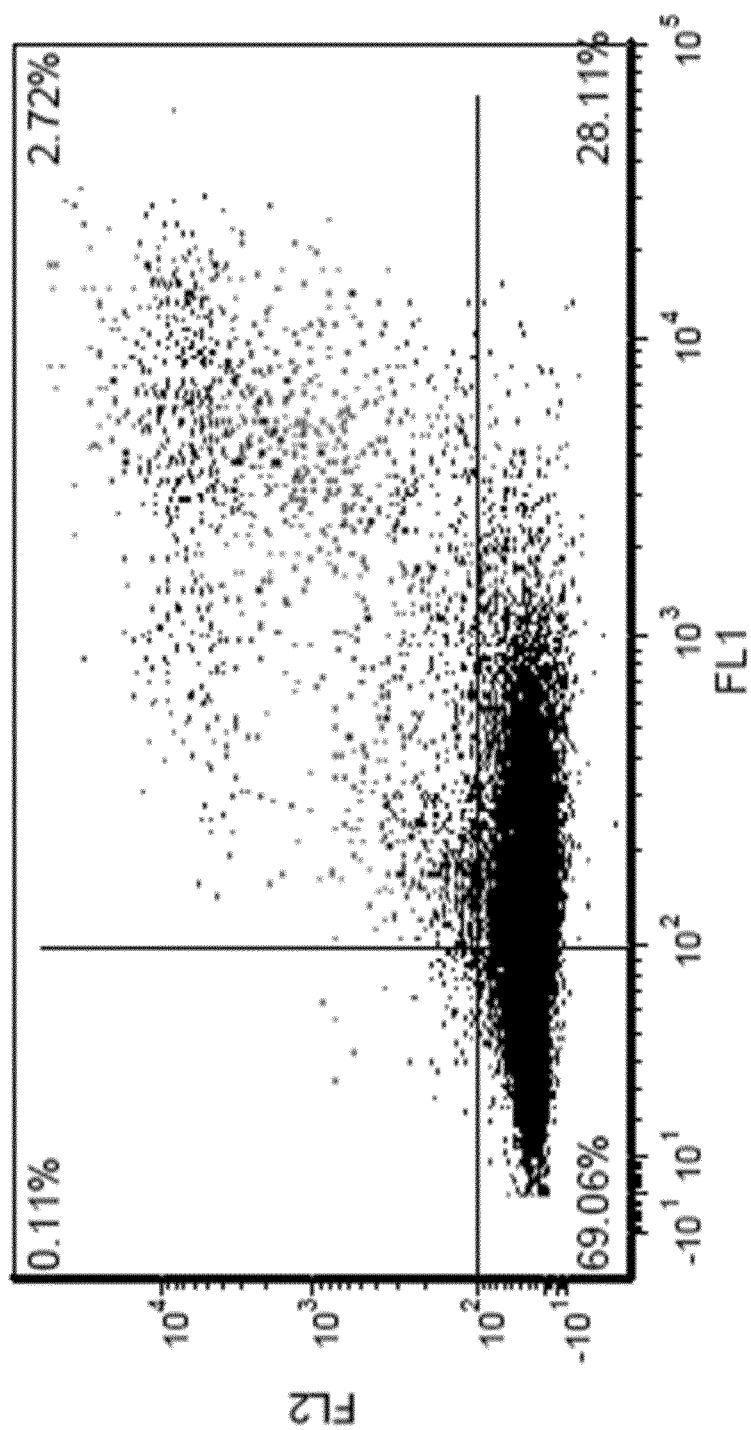
Figure 14E:
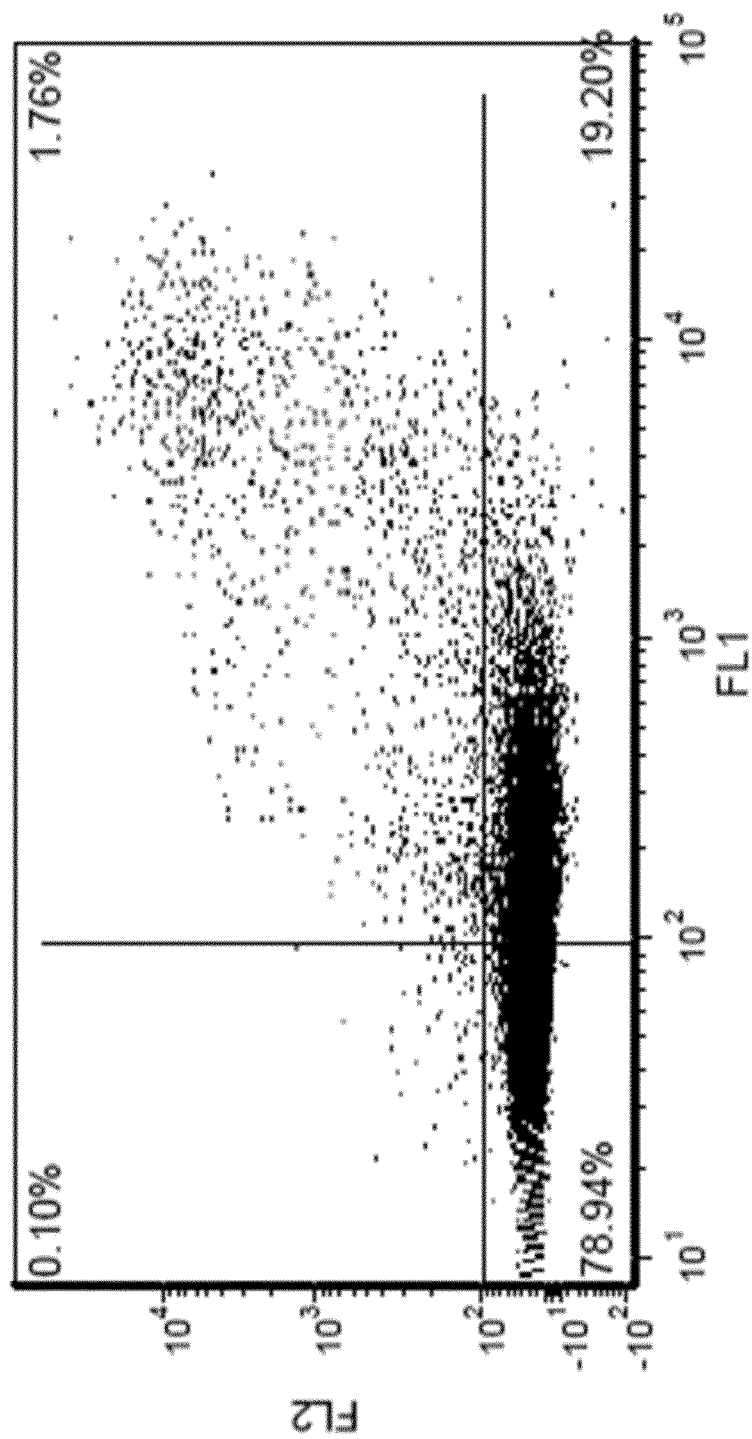
Figure 15A:
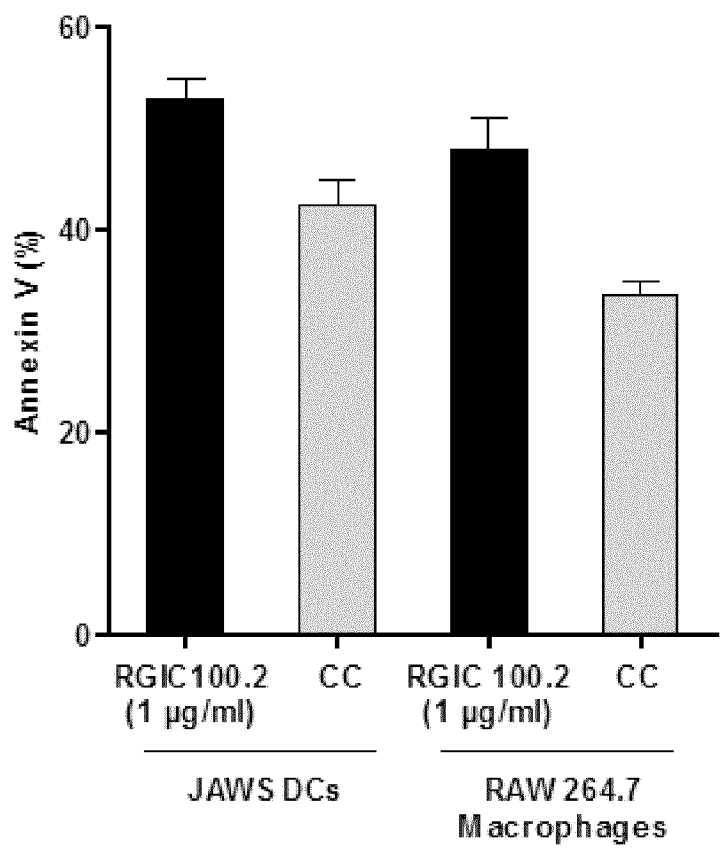
Figure 15B:
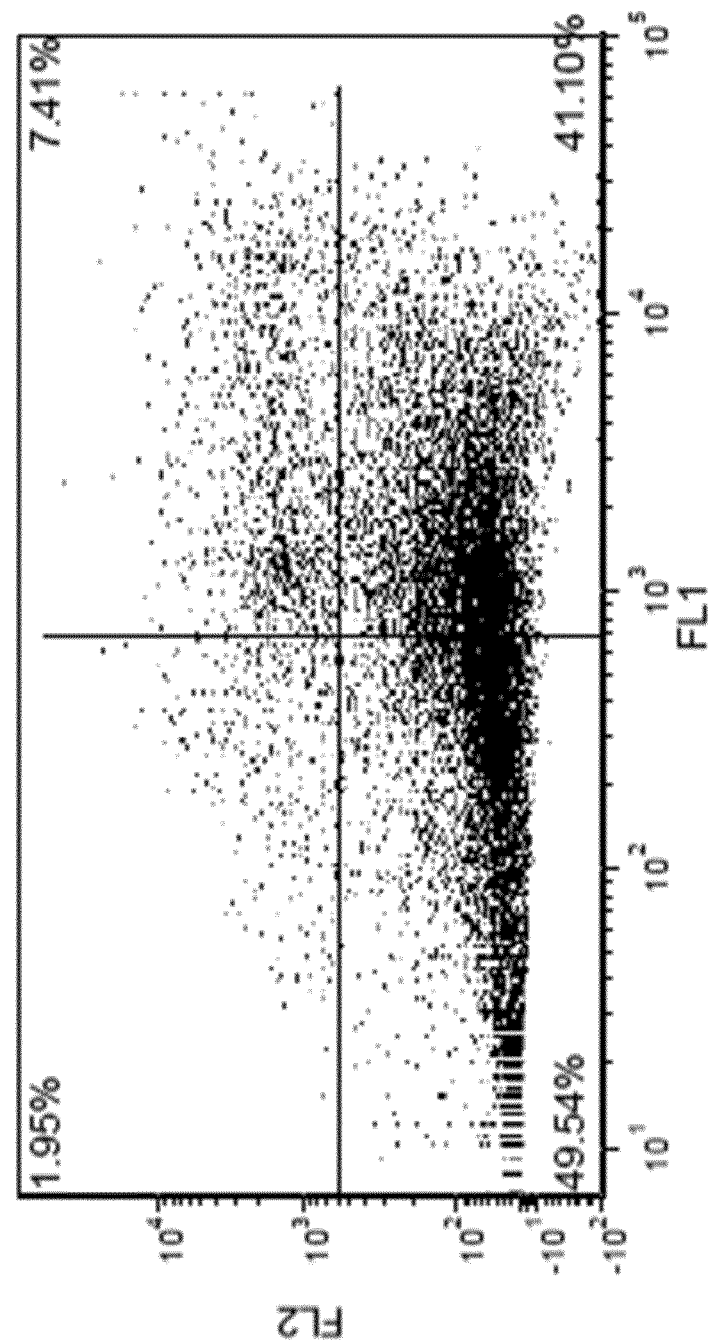
Figure 15C:
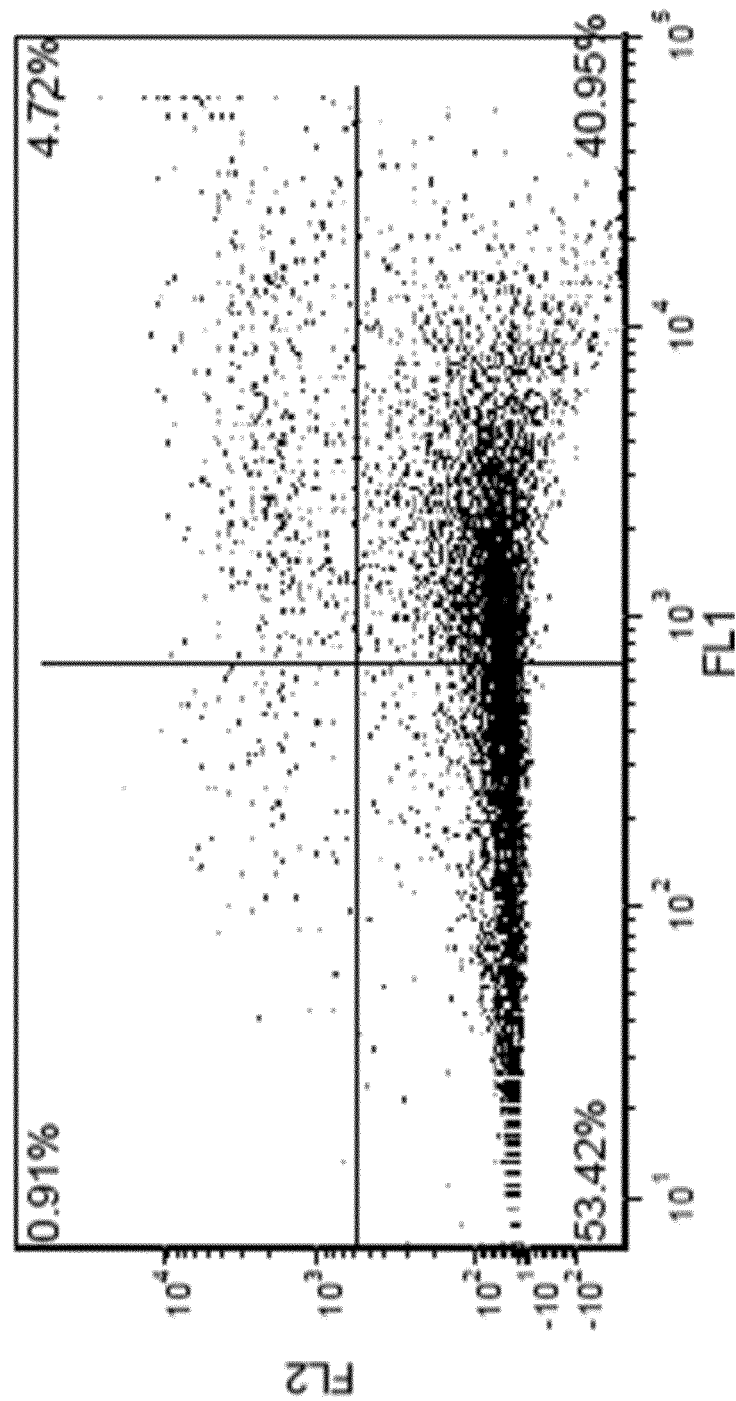
Figure 15D:
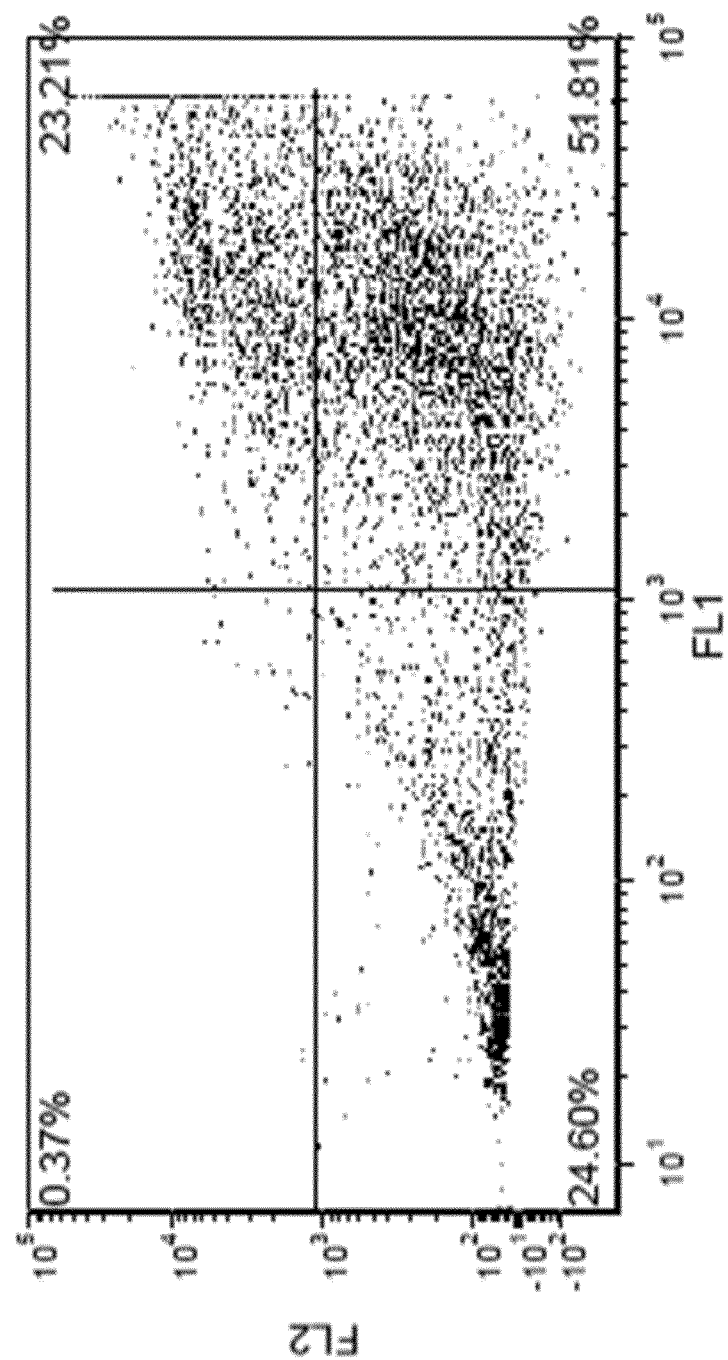
Figure 15E:
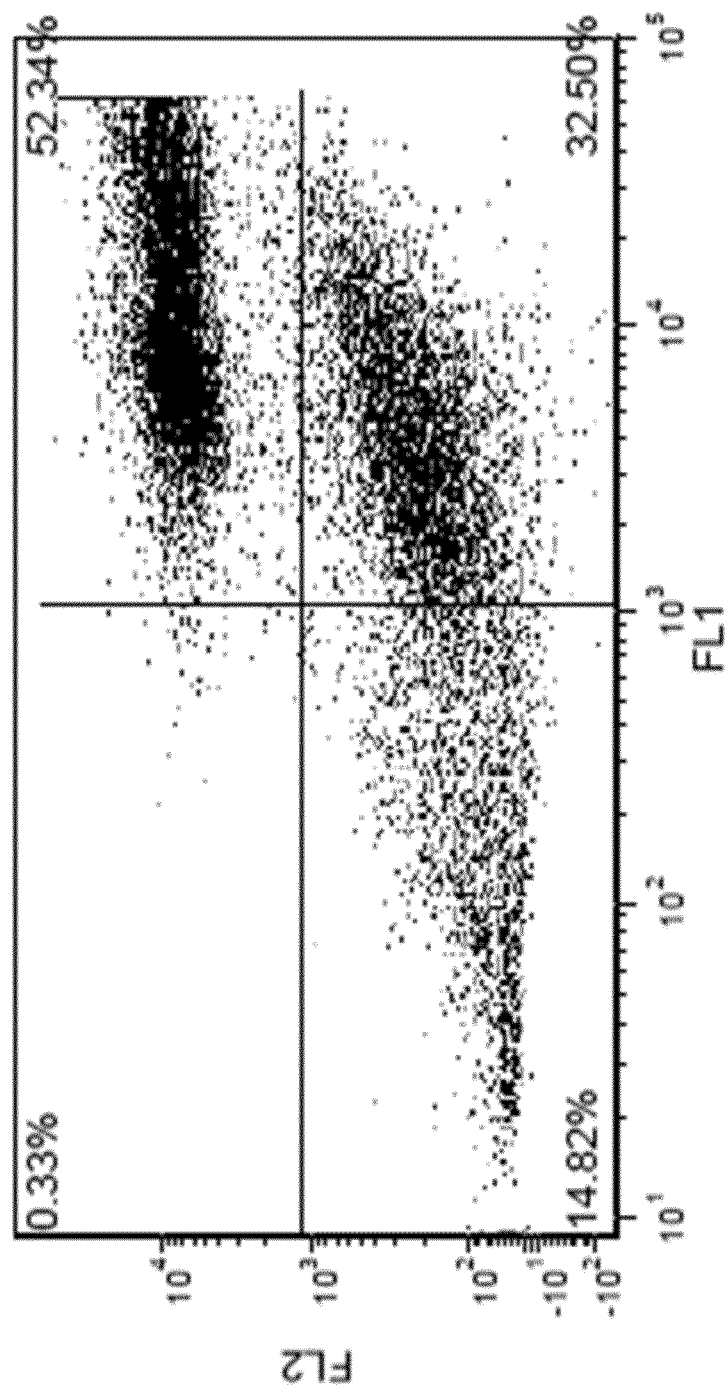
Figure 16A:
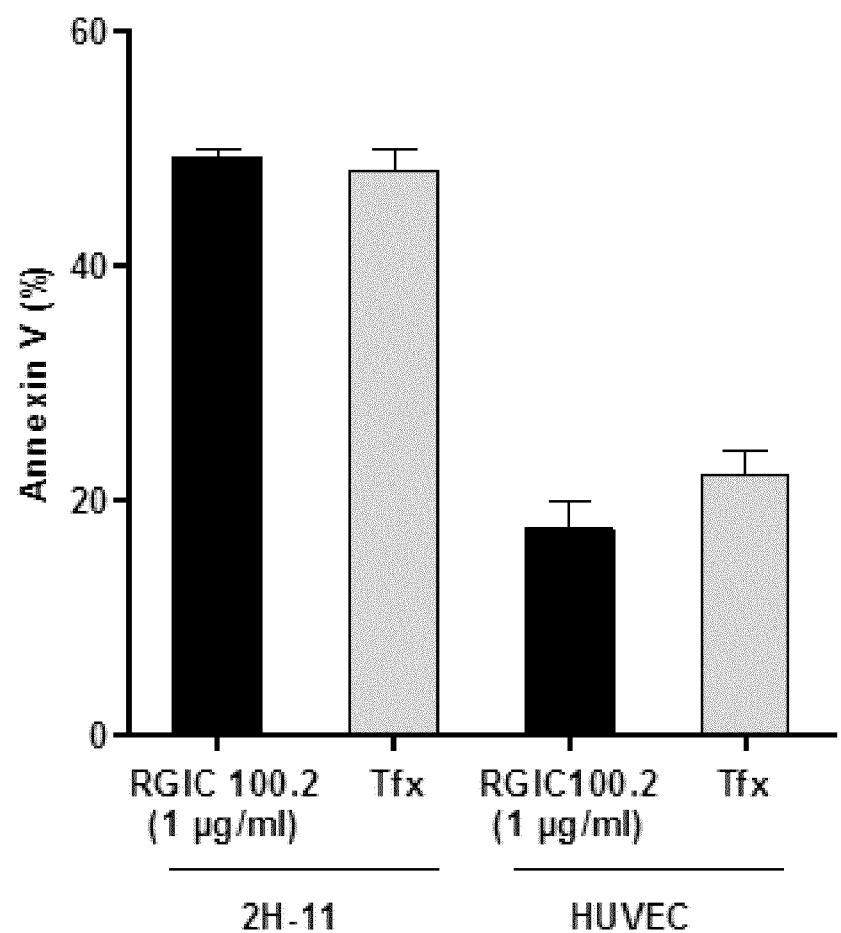
Figure 16B:
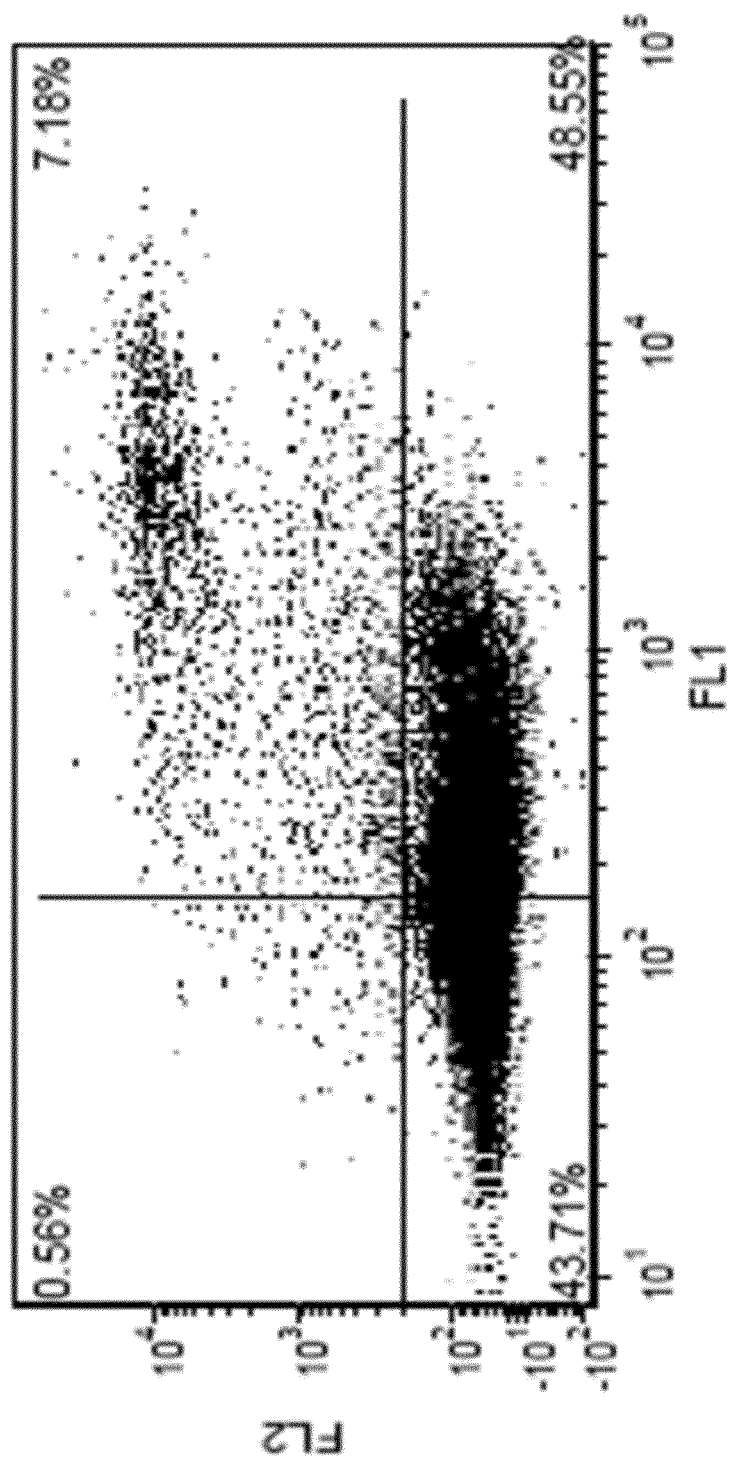
Figure 16C:
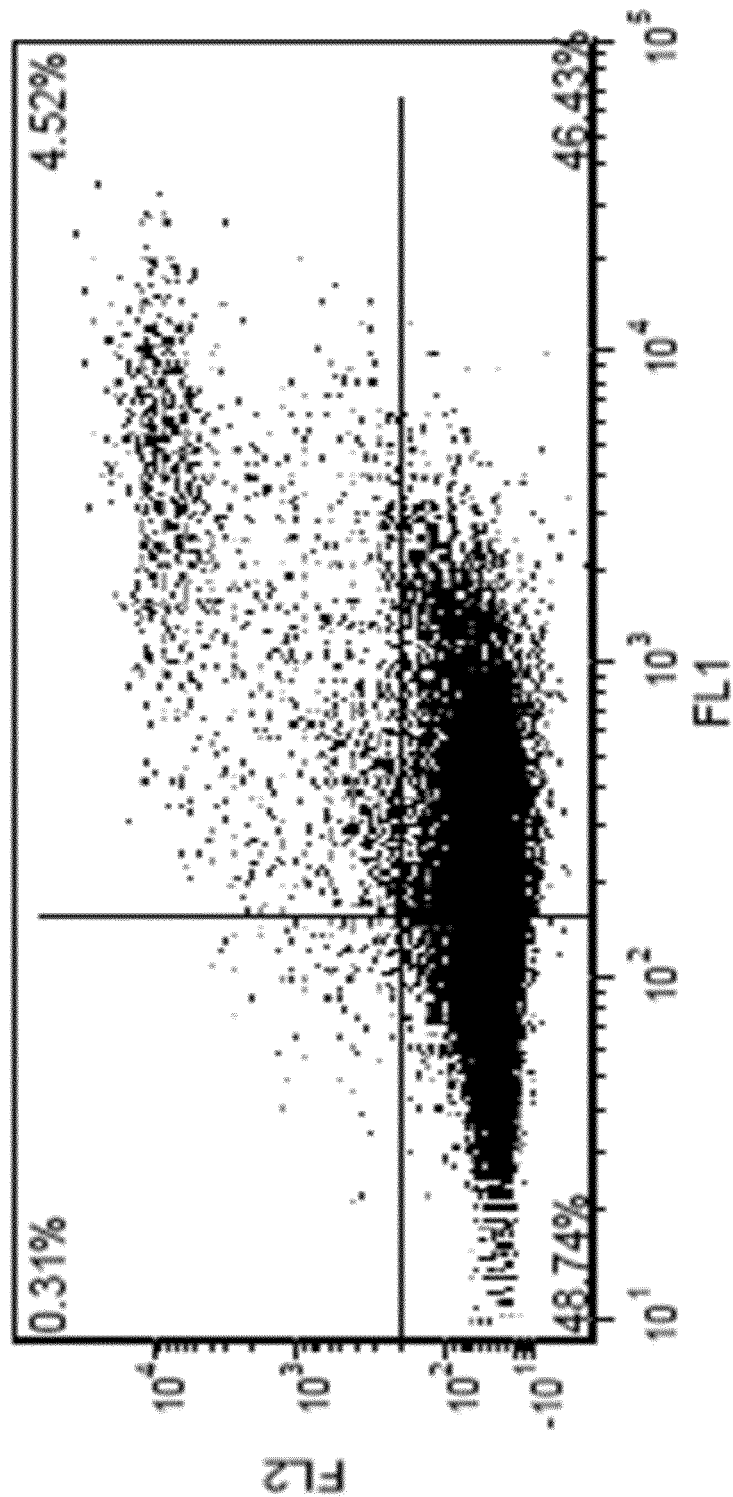
Figure 16D:
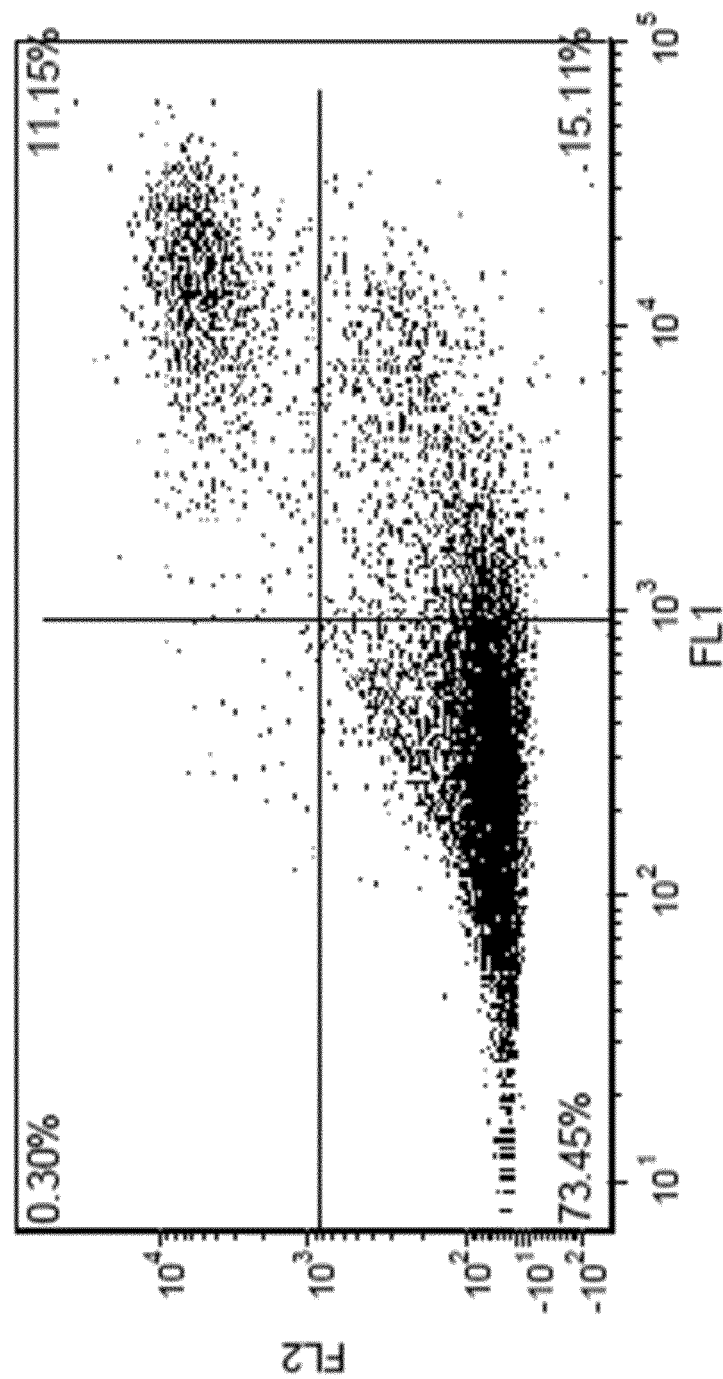
Figure 16E:
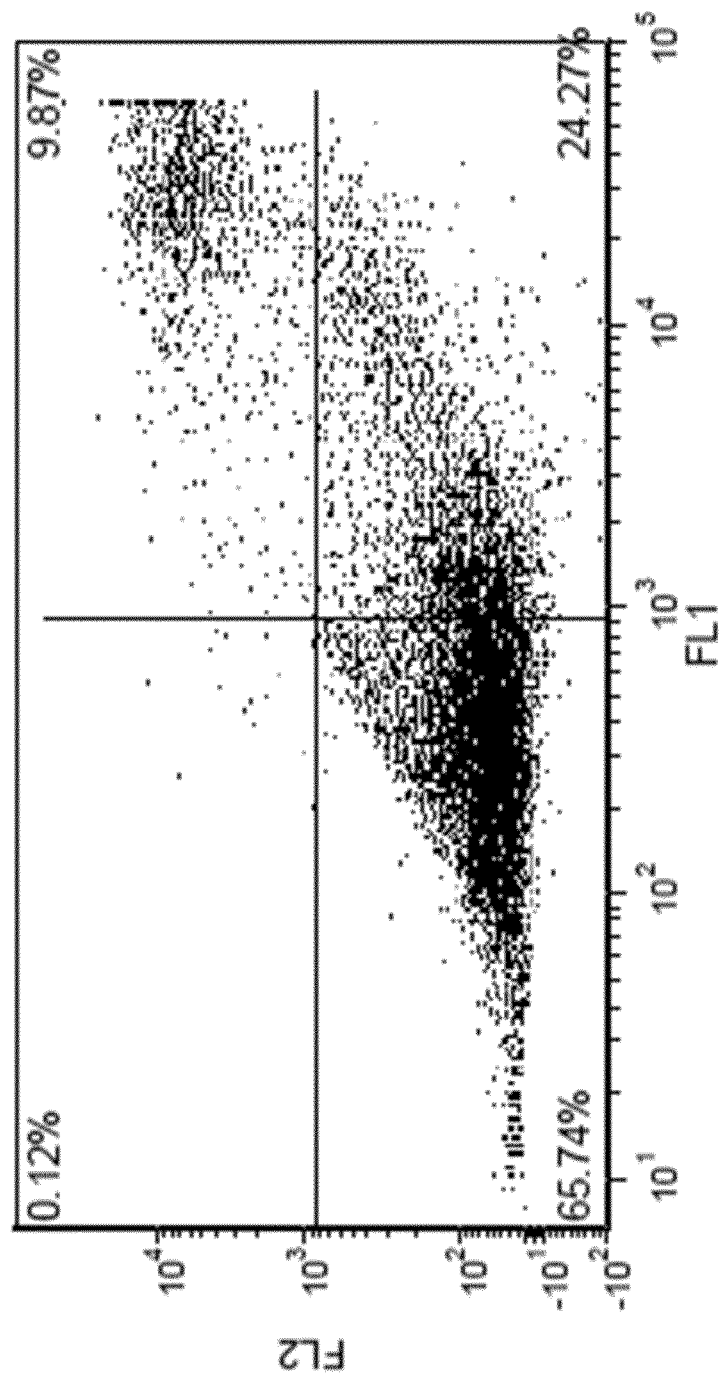

Cells were plated in round-bottomed 96-well plates at $5\times10^4$ cells/well. The cells were incubated with the dsRNA compositions RGIC 100.1, RGIC 100.2 and RGIC 100.3 at different concentrations as indicated in FIG. 13A (RGIC 100.1), FIG. 13B (RGIC 100.2) and FIG. 13C (RGIC 100.3), respectively. For comparison, a poly(I:C) reagent (HMW-polyIC; InvivoGen, San Diego, Calif., USA) at a concentration of 10 µg/ml was used.

After 16 h incubation, cell supernatants were collected and SEAP levels were measured using the QUANTI-Blue™ kit (InvivoGen, San Diego, Calif., USA) according to the manufacturer's instructions.

In this way, the $B_{max}$ and $K_D$ values were determined for each dsRNA composition as outlined in the above legend to FIG. 13.

Example 6: dsRNA Compositions According to the Invention Show a Pro-Apoptotic Activity on Cancer Cells but not on Non-Tumor Cells HeLa cells, JAWS II DCs, RAW 264.7 macrophages, 2H-11 endothelial cells or HUVECs were plated in round-bottomed 96-well plates at $5\times10^4$ cells/well. The cells were incubated with the dsRNA composition RGIC 100.2 at a concentration of 5 µg/ml or 1 µg/ml. Cells were analysed by FACS using channel FL1 for annexin V, and channel FL2 for propidium iodide. The results of the cytometry analyses are shown in FIG. 14 (HeLa), FIG. 15 (immune cells: JAWS II DCs and RAW 264.7 macrophages) and FIG. 16 (non-immune cells: 2H-11 endothelial cells and HUVECs). Only cancer cells (HeLa) respond to RIGC 100.2 treatment with significant apoptosis.

In summary, the present invention provides novel dsRNAs and compositions thereof as TLR3 agonists. The dsRNAs and compositions thereof have a defined chemical structure and molecular weight (particularly in contrast to poly(I:C) reagents). dsRNAs of the invention activate DCs and macrophages in a dose-dependent manner. In certain embodiments, activation of immune cells by dsRNAs of the invention is even higher than that exerted by poly(I:C). A higher inosine content in the inventive dsRNAs leads to a stronger activation of immune cells. However, when the inosine content (in mol-%) is identical between two different dsRNAs or two different dsRNA composition, respectively, activation of immune cells relates to the length of the dsRNAs (the length of the dsRNAs is proportional to the activation of the immune cells); see FIG. 12. The highly beneficial properties of dsRNAs of the invention as anti-tumor or anti-cancer drugs are underscored by their anti-apoptotic activity which is specific for cancer or tumor cells (compare FIG. 14 with FIGS. 15 and 16).

The invention claimed is:

1. A double-stranded ribonucleic acid (dsRNA) of at least 45 bp wherein one strand is essentially polycytidylic acid and the complementary strand essentially contains guanosyl and inosinyl according to the formula $(G)_{1\ to\ (n-1)}I_{(n-1)\ to\ 1}$ with n being the total number of nucleotides in the complementary strand, and wherein the guanosine and inosine residues can have any position in the sequence of the complementary strand.

2. The dsRNA of claim 1 wherein at least one strand has a free 5' triphosphate group.

3. The dsRNA of claim 2 wherein the complementary strand containing the guanosine and inosine residues has a free 5' triphosphate group.

4. The dsRNA according to claim 1 having a length of from 50 to 200 bp.

5. The dsRNA according to claim 1 conjugated to a ligand selected from the group consisting of dyes, fluorescent labels, antigens, antibodies and antibody fragments.

6. A composition comprising at least two different dsRNAs of at least 45 bp wherein one strand is essentially polycytidylic acid and the complementary strand essentially contains guanosyl and inosinyl according to the formula $(G)_{1\ to\ (n-1)}I_{(n-1)\ to\ 1}$ with n being the total number of nucleotides in the complementary strand, and wherein the guanosine and inosine residues can have any position in the sequence of the complementary strand, said different dsRNAs having one or more of a different base composition in the complementary strand and a different length.

7. The composition of claim 6 wherein the accumulated base composition (in mol-%) of the dsRNAs in said pool is 50% cytosine (C), from 1 to 49% guanosine (G), and the remainder inosine (I).

8. The composition of claim 7 wherein the base composition is 50% C, from 10 to 40% G, and the remainder I.

9. The composition according to claim 6 wherein the percentage of I is greater than the percentage of G.

10. A method for the preparation of a composition comprising at least two different dsRNAs of at least 45 bp wherein one strand is essentially polycytidylic acid and the complementary strand essentially contains guanosyl and inosinyl according to the formula $(G)_{1\ to\ (n-1)}I_{(n-1)\ to\ 1}$ with n being the total number of nucleotides in the complementary strand, and wherein the guanosine and inosine residues can have any position in the sequence of the complementary strand, said different dsRNAs having one or more of a different base composition in the complementary strand and a different length, comprising the step of incubating a single-stranded poly cytidyl RNA template with an RNA-dependent RNA polymerase from a virus of the Caliciviridae family in the presence of a mixture of rGTP and rITP, and optionally rCTP.

11. The method of claim 10 wherein the molar ratio of rGTP to rITP in said mixture is from 1:10 to 10:1.

12. A pharmaceutical composition comprising one or more double-stranded ribonucleic acid (dsRNA) of at least 45 bp wherein one strand is essentially polycytidylic acid and the complementary strand essentially contains guanosyl and inosinyl according to the formula $(G)_{1\ to\ (n-1)}I_{(n-1)\ to\ 1}$ with n being the total number of nucleotides in the complementary strand, and wherein the guanosine and inosine residues can have any position in the sequence of the complementary strand, in combination with at least one pharmaceutically acceptable carrier, excipient and/or diluent.

13. The pharmaceutical composition of claim 12 further comprising an antigen.

14. The pharmaceutical composition of claim 12 further comprising an adjuvant.

15. The pharmaceutical composition according to claim 12 comprising at least one further immunomodulatory agent, immunostimulatory agent, and/or therapeutic or prophylactic vaccine and/or least one anti-cancer or anti-tumor drug and/or at least one drug for immunotherapy.

16. A method of activation of Toll-like receptor 3 (TLR3) by administering an effective amount of a pharmaceutical composition comprising one or more double-stranded ribonucleic acid (dsRNA) of at least 45 bp wherein one strand is essentially polycytidylic acid and the complementary strand essentially contains guanosyl and inosinyl according to the formula $(G)_{1\ to\ (n-1)}I_{(n-1)\ to\ 1}$ with n being the total number of nucleotides in the complementary strand, and wherein the guanosine and inosine residues can have any position in the sequence of the complementary strand, in combination with at least one pharmaceutically acceptable carrier, excipient and/or diluent, to the Toll-like receptor 3 (TLR3).

17. The method of claim 16 wherein the method is conducted in vitro.

18. The method of claim 16 wherein the pharmaceutical composition is administered to a subject by sub-cutaneous, intra-muscular, intra-dermal, inter-thecal, intra-occular and/or intra-venous injection in a single or repeated dose, to activate Toll-like receptor 3 (TLR3).

19. A method of immunostimulation by activation of dendritic cells, macrophages, or monocytes via Toll-like receptor 3 (TLR3), comprising administering an effective amount of a pharmaceutical composition comprising one or more double-stranded ribonucleic acid (dsRNA) of at least 45 bp wherein one strand is essentially polycytidylic acid and the complementary strand essentially contains guanosyl and inosinyl according to the formula $(G)_{1\ to\ (n-1)}I_{(n-1)\ to\ 1}$ with n being the total number of nucleotides in the complementary strand, and wherein the guanosine and inosine residues can have any position in the sequence of the complementary strand, in combination with at least one pharmaceutically acceptable carrier, excipient and/or diluent, to dendritic cells, macrophages, or monocytes having Toll-like receptor 3 (TLR3).

20. The method of claim 19 wherein the method is conducted in vitro.

21. The method of claim 19 wherein the pharmaceutical composition is administered to a subject by sub-cutaneous, intra-muscular, intra-dermal, inter-thecal, intra-occular and/or intra-venous injection in a single or repeated dose, to activate dendritic cells, macrophages, or monocytes via Toll-like receptor 3 (TLR3).

22. A method of stimulating production of IL-6 in dendritic cells via Toll-like receptor 3 (TLR3), comprising administering an effective amount of a pharmaceutical composition comprising one or more double-stranded ribonucleic acid (dsRNA) of at least 45 bp wherein one strand is essentially polycytidylic acid and the complementary strand essentially contains guanosyl and inosinyl according to the formula $(G)_{1\ to\ (n-1)}I_{(n-1)\ to\ 1}$ with n being the total number of nucleotides in the complementary strand, and wherein the guanosine and inosine residues can have any position in the sequence of the complementary strand, in combination with at least one pharmaceutically acceptable carrier, excipient and/or diluent, to dendritic cells having Toll-like receptor 3 (TLR3).

23. The method of claim 22 wherein the method is conducted in vitro.

24. The method of claim 22 wherein the pharmaceutical composition is administered to a subject by sub-cutaneous, intra-muscular, intra-dermal, inter-thecal, intra-occular and/or intra-venous injection in a single or repeated dose, to activate dendritic cells via Toll-like receptor 3 (TLR3).

25. A method of stimulating production of TNF-α in macrophages via Toll-like receptor 3 (TLR3), comprising administering an effective amount of a pharmaceutical composition comprising one or more double-stranded ribonucleic acid (dsRNA) of at least 45 bp wherein one strand is essentially polycytidylic acid and the complementary strand essentially contains guanosyl and inosinyl according to the formula $(G)_{1\ to\ (n-1)}I_{(n-1)\ to\ 1}$ with n being the total number of nucleotides in the complementary strand, and wherein the guanosine and inosine residues can have any position in the sequence of the complementary strand, in combination with at least one pharmaceutically acceptable carrier, excipient and/or diluent, to macrophages having Toll-like receptor 3 (TLR3).

26. The method of claim 25 wherein the method is conducted in vitro.

27. The method of claim 25 wherein the pharmaceutical composition is administered to a subject by sub-cutaneous, intra-muscular, intra-dermal, inter-thecal, intra-occular and/or intra-venous injection in a single or repeated dose, to activate dendritic cells via Toll-like receptor 3 (TLR3).

28. A method of inducing apoptosis in cervical cancer cells, comprising administering an effective amount of a pharmaceutical composition comprising one or more double-stranded ribonucleic acid (dsRNA) of at least 45 bp wherein one strand is essentially polycytidylic acid and the complementary strand essentially contains guanosyl and inosinyl according to the formula $(G)_{1\ to\ (n-1)}I_{(n-1)\ to\ 1}$ with n being the total number of nucleotides in the complementary strand, and wherein the guanosine and inosine residues can have any position in the sequence of the complementary strand, in combination with at least one pharmaceutically acceptable carrier, excipient and/or diluent, to cervical cancer cells having Toll-like receptor 3 (TLR3).

29. The method of claim 28 wherein the method is conducted in vitro.

30. The method of claim 28 wherein the pharmaceutical composition is administered to a subject by sub-cutaneous, intra-muscular, intra-dermal, inter-thecal, intra-occular and/or intra-venous injection in a single or repeated dose, to inducing apoptosis in cervical cancer cells.

\* \* \* \* \*

SEQUENCE LISTING

<160> NUMBER OF SEQ ID NOS: 1

<210> SEQ ID NO 1
<211> LENGTH: 21
<212> TYPE: DNA
<213> ORGANISM: Homo sapiens

```
<220> FEATURE:
<221> NAME/KEY: source
<222> LOCATION: 1..21
<223> OTHER INFORMATION: /mol_type="DNA"
      /note="Sequence of TLR-3 targeted with siRNA of Example 4"
      /organism="Homo sapiens"

<400> SEQUENCE: 1
ctcggcctta atgaaattga a                                                    21
```